(12) United States Patent
Kostrzewski et al.

(10) Patent No.: US 9,241,771 B2
(45) Date of Patent: Jan. 26, 2016

(54) NOTCHED APPARATUS FOR GUIDANCE OF AN INSERTABLE INSTRUMENT ALONG AN AXIS DURING SPINAL SURGERY

(71) Applicant: KB Medical SA, Ecublens (CH)

(72) Inventors: Szymon Kostrzewski, Lausanne (CH); Billy Nussbaumer, Préverenges (CH); Roderik Berthelin, La Chapelle Rambaud (FR); Chetan K. Patel, Altamonte Springs, FL (US)

(73) Assignee: KB Medical SA (CH)

( * ) Notice: Subject to any disclaimer, the term of this patent is extended or adjusted under 35 U.S.C. 154(b) by 0 days.

(21) Appl. No.: 14/597,883

(22) Filed: Jan. 15, 2015

(65) Prior Publication Data

US 2015/0196365 A1 Jul. 16, 2015

Related U.S. Application Data

(60) Provisional application No. 61/953,609, filed on Mar. 14, 2014, provisional application No. 61/935,281, filed on Feb. 3, 2014, provisional application No. 61/927,894, filed on Jan. 15, 2014.

(51) Int. Cl.
  *A61B 19/00* (2006.01)
  *A61B 17/17* (2006.01)
  *A61B 17/34* (2006.01)

(52) U.S. Cl.
  CPC ............. *A61B 19/2203* (2013.01); *A61B 17/17* (2013.01); *A61B 17/3417* (2013.01); *A61B 19/201* (2013.01); *A61B 19/5244* (2013.01); *A61B 19/54* (2013.01); *A61B 17/1703* (2013.01); *A61B 2019/2223* (2013.01); *A61B 2019/2234* (2013.01); *A61B 2019/5255* (2013.01); *A61B2019/5291* (2013.01); *A61B 2019/5297* (2013.01); *A61B 2019/5437* (2013.01)

(58) Field of Classification Search
  CPC ............... A61B 17/17; A61B 17/1703; A61B 2019/2223; A61B 19/2203
  See application file for complete search history.

(56) References Cited

U.S. PATENT DOCUMENTS 5,408,409 A 4/1995 Glassman et al.
5,948,002 A * 9/1999 Bonutti .......................... 606/232

(Continued)

FOREIGN PATENT DOCUMENTS

EP          1693011 A1    8/2006
WO    WO-2005/122916 A1    12/2005

(Continued)

OTHER PUBLICATIONS

Rosa Is a New Stereotactic Neurological Surgery Robot, Neurological Surgery, Jun. 13, 2011 (http://www.medgadget.com/2011/06/rosa-neuro-surgery-robot.html).

*Primary Examiner* — Andrew Yang
(74) *Attorney, Agent, or Firm* — Choate, Hall & Stewart LLP; William R. Haulbrook

(57) ABSTRACT

Described herein is a surgical instrument guide for use with a robotic surgical system, for example, during spinal surgery. In certain embodiments, the guide is attached to or is part of an end effector of a robotic arm, and provides a rigid structure that allows for precise preparation of patient tissue (e.g., preparation of a pedicle) by drilling, tapping, or other manipulation, as well as precise placement of a screw in a drilled hole or affixation of a prosthetic or implant in a prepared patient situation.

11 Claims, 20 Drawing Sheets

(56) References Cited

U.S. PATENT DOCUMENTS

| | | |
|---|---|---|
| 8,509,503 B2 | 8/2013 | Nahum et al. |
| 2003/0097060 A1 | 5/2003 | Yanof et al. |
| 2005/0245817 A1 | 11/2005 | Clayton et al. |
| 2006/0161136 A1 | 7/2006 | Anderson et al. |
| 2007/0055291 A1 | 3/2007 | Birkmeyer et al. |
| 2007/0156157 A1 | 7/2007 | Nahum et al. |
| 2008/0215181 A1 | 9/2008 | Smith et al. |
| 2008/0221520 A1 | 9/2008 | Nagel et al. |
| 2009/0088848 A1 | 4/2009 | Martz et al. |
| 2010/0210939 A1 | 8/2010 | Hartmann et al. |
| 2011/0082462 A1 | 4/2011 | Suarez et al. |
| 2011/0126844 A1 | 6/2011 | Cinquin et al. |
| 2013/0113798 A1 | 5/2013 | Nahum et al. |
| 2013/0172902 A1 | 7/2013 | Lightcap et al. |
| 2013/0317344 A1 | 11/2013 | Borus et al. |
| 2014/0052151 A1 | 2/2014 | Hingwe et al. |
| 2014/0121676 A1 | 5/2014 | Kostrzewski et al. |
| 2015/0045813 A1 | 2/2015 | Kostrzewski et al. |
| 2015/0100066 A1 | 4/2015 | Kostrzewski et al. |
| 2015/0202009 A1 | 7/2015 | Nussbaumer et al. |

FOREIGN PATENT DOCUMENTS

| | | |
|---|---|---|
| WO | WO-2006/091494 A1 | 8/2006 |
| WO | WO-2007/136768 A2 | 11/2007 |
| WO | WO-2008/097540 A2 | 8/2008 |
| WO | WO-2009/013406 A2 | 1/2009 |
| WO | WO-2013/079843 A1 | 6/2013 |
| WO | WO-2013/098496 A1 | 7/2013 |
| WO | WO-2015/049109 A1 | 4/2015 |

\* cited by examiner

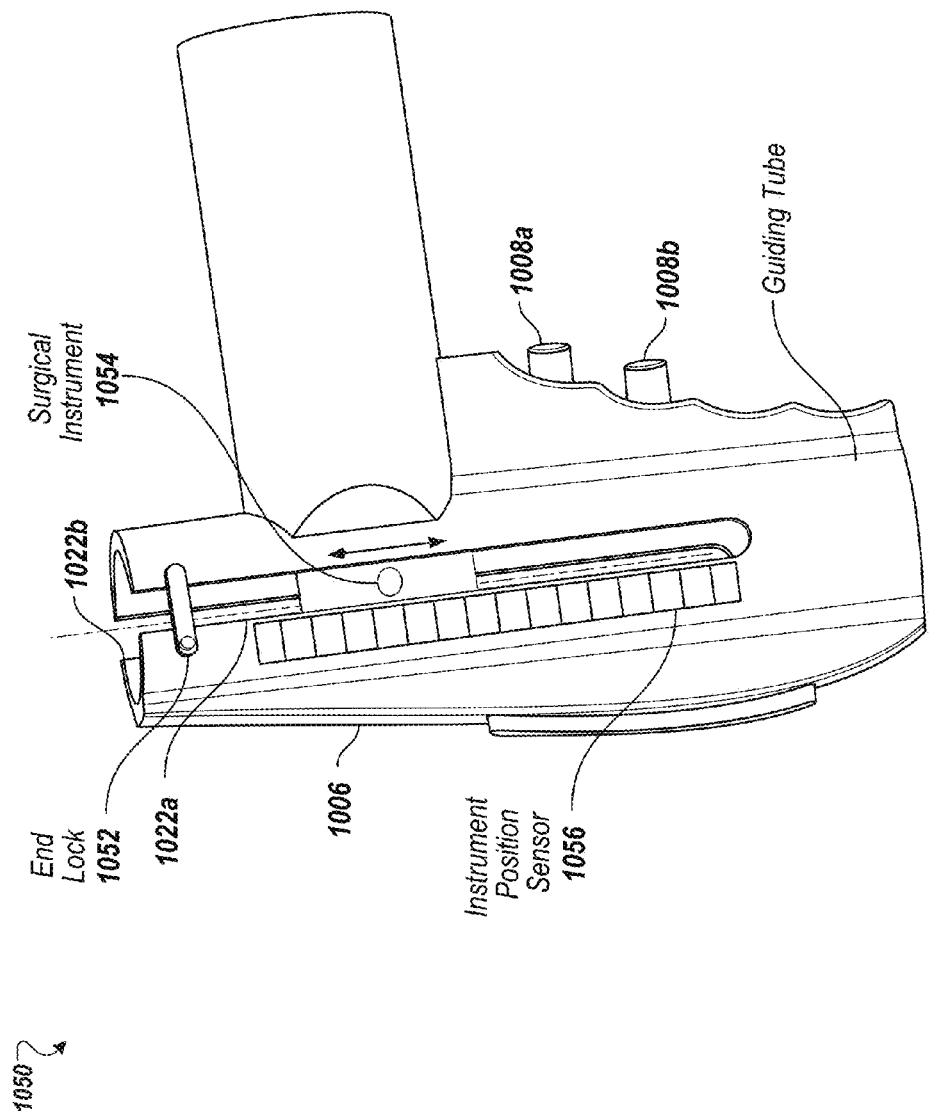

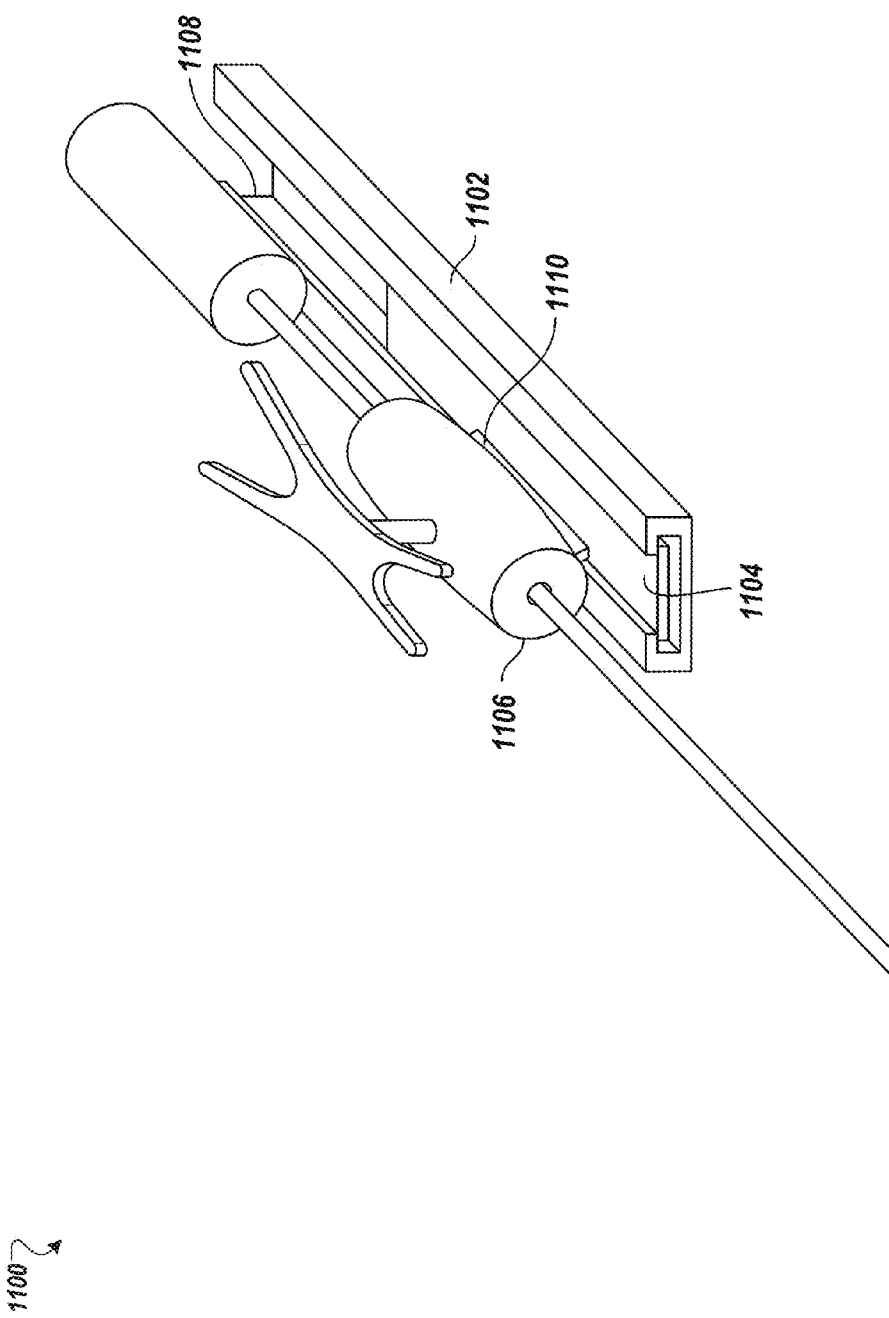

NOTCHED APPARATUS FOR GUIDANCE OF AN INSERTABLE INSTRUMENT ALONG AN AXIS DURING SPINAL SURGERY

RELATED APPLICATIONS

The present application claims priority to U.S. Provisional Application No. 61/927,894, filed Jan. 15, 2014; U.S. Provisional Application No. 61/935,281, filed Feb. 3, 2014; and U.S. Provisional Application No. 61/953,609, filed Mar. 14, 2014, the contents of each of which are hereby incorporated by reference in their entireties.

BACKGROUND

Robotic-assisted surgical systems have been developed to improve surgical precision and enable the implementation of new surgical procedures. For example, robotic systems have been developed to sense a surgeon's hand movements and translate them to scaled-down micro-movements and filter out unintentional tremors for precise microsurgical techniques in organ transplants, reconstructions, and minimally invasive surgeries. Other robotic systems are directed to telemanipulation of surgical tools such that the surgeon does not have to be present in the operating room, thereby facilitating remote surgery. Feedback-controlled robotic systems have also been developed to provide smoother manipulation of a surgical tool during a procedure than could be achieved by an unaided surgeon.

However, widespread acceptance of robotic systems by surgeons and hospitals is limited for a variety of reasons. Current systems are expensive to own and maintain. They often require extensive preoperative surgical planning prior to use, and they extend the required preparation time in the operating room. They are physically intrusive, possibly obscuring portions of a surgeons field of view and blocking certain areas around the operating table, such that a surgeon and/or surgical assistants are relegated to one side of the operating table. Current systems may also be non-intuitive or otherwise cumbersome to use, particularly for surgeons who have developed a special skill or "feel" for performing certain maneuvers during surgery and who find that such skill cannot be implemented using the robotic system. Finally, robotic surgical systems may be vulnerable to malfunction or operator error, despite safety interlocks and power backups.

Spinal surgeries often require precision drilling and placement of screws or other implements in relation to the spine, and there may be constrained access to the vertebrae during surgery that makes such maneuvers difficult. Catastrophic damage or death may result from improper drilling or maneuvering of the body during spinal surgery, due to the proximity of the spinal cord and arteries. Common spinal surgical procedures include a discectomy for removal of all or part of a disk, a foraminotomy for widening of the opening where nerve roots leave the spinal column, a laminectomy for removal of the lamina or bone spurs in the back, and spinal fusion for fusing of two vertebrae or vertebral segments together to eliminate pain caused by movement of the vertebrae.

Spinal surgeries that involve screw placement require preparation of holes in bone (e.g., vertebral segments) prior to placement of the screws. Where such procedures are performed manually, in some implementations, a surgeon judges a drill trajectory for subsequent screw placement on the basis of pre-operative CT scans. Other manual methods which do not involve usage of the pre-operative CT scans, such as fluoroscopy, 3D fluoroscopy or natural landmark-based, may be used to determine the trajectory for preparing holes in bone prior to placement of the screws. In some implementations, the surgeon holds the drill in his hand while drilling, and fluoroscopic images are obtained to verify if the trajectory is correct. Some surgical techniques involve usage of different tools, such as a pedicle finder or K-wires. Such procedures rely strongly on the expertise of the surgeon, and there is significant variation in success rate among different surgeons. Screw misplacement is a common problem in such surgical procedures.

Image-guided spinal surgeries involve optical tracking to aid in screw placement. However, such procedures are currently performed manually, and surgical tools can be inaccurately positioned despite virtual tracking. A surgeon is required to coordinate his real-world, manual manipulation of surgical tools using images displayed on a two dimensional screen. Such procedures can be non-intuitive and require training, since the surgeon's eye must constantly scan both the surgical site and the screen to confirm alignment. Furthermore, procedural error can result in registration inaccuracy of the image-guiding system, rendering it useless, or even misleading.

Certain force feedback systems are used by surgeons in certain procedures; however such systems have a large footprint and take up valuable, limited space in the operating room. These systems also require the use of surgical tools that are specially adapted for use with the force feedback system, and the training required by surgeons to operate such systems can be significant. Moreover, surgeons may not be able to use expertise they have developed in performing spinal surgeries when adapting to use of the current force feedback systems. Such systems, while precise, may require more surgical time and more operating room preparation time to ready placement of the equipment for surgery. Thus, there is a need for systems, apparatus, and methods that provide enhanced precision in performing surgeries such as spinal surgeries.

SUMMARY

Described herein is a surgical instrument guide for use with a robotic surgical system, for example, during spinal surgery. In certain embodiments, the guide is attached to or is part of an end effector of a robotic arm, and provides a rigid structure that allows for precise preparation of patient tissue (e.g., preparation of a pedicle) by drilling, tapping, or other manipulation, as well as precise placement of a screw in a drilled hole or affixation of a prosthetic or implant in a prepared patient situation.

In certain embodiments, the guide has a tubular shape with a longitudinal notch along a portion of its length. The notch is sized to allow a surgical instrument to slide through the guide in a fixed orientation while the guide is held by the robotic arm at a desired, fixed trajectory in relation to the patient. In some implementations, the guide has more than one notch (e.g., two notches). Among other things, incorporation of two or more notches permits ambidextrous manipulation of the end effector and/or tool.

The surgical instrument, in some implementations, is fitted with a tool support having a navigational marker (e.g., a multipoint, planar marker) attached thereto via a peg sized to fit in the notch. In some implementations, the peg is utilized without the navigation marker to maintain the orientation of the surgical instrument. The tool support constrainably slides along at least a portion of the guide interior. The guide restricts the movement of the tool support (and hence the surgical instrument) as the surgical instrument slides along the interior of the guide. Thus, because of the notch, movement of the marker is constrained in a fixed orientation as it slides along the axis defined by the guide, e.g., the marker cannot rotate about the axis along which movement of the surgical tool is constrained. This facilitates and simplifies tracking of the marker, e.g., via a remote tracking system that displays real-time tracking of the surgical instrument during the surgical procedure.

The guide, in some implementations, also allows better control and maneuverability of the surgical tool, since rotation of the tool is disallowed (e.g., by the notch in the guide and the peg on the tool support) as the surgeon slides it through the guide along the fixed trajectory. Furthermore, the guide still allows the robotic arm to compensate for a force or torque applied by the surgeon, maintaining the fixed trajectory in relation to the patient despite the applied force or torque.

The disclosed technology, in certain embodiments, includes a surgical instrument guide for use with a robotic surgical system. The surgical instrument guide may include a rigid hollow tubular structure having a first open end and a second open end that define an axis along which movement of a surgical instrument (fitted with a tool support) sliding through the structure is restricted. The tubular structure (e.g., a cylindrical structure) may have an interior surface shaped and sized to accommodate the tool support sliding through the guide such that movement of the tool support is constrained in all directions except along the axis defined by the guide. The tubular structure may have an exterior surface comprising at least one flange that is configured for secure coupling of the guide to an end effector of the robotic surgical system. In certain embodiments, the tubular structure includes a longitudinal notch (e.g., a slot) along its length that is sized in relation to a peg to (i) permit a navigation marker attached to the tool support via the peg to be viewable by a navigation camera along an entire range of movement of the tool support through the guide, (ii) constrain movement of the marker in a fixed orientation along the axis defined by the guide, and (ii) permit the tool support to slide along the axis defined by the guide while the guide is held in a fixed position by the robotic surgical system. The navigation marker may be used by navigation camera to track the surgical instrument. The navigation marker may be, for example, navigation tracker such as the Dedicated NavLock™ tracker from Medtronic, Inc. of Minneapolis, Minn.

The longitudinal notch may be sized in relation to a peg to permit the surgical instrument to slide along the axis of insertion in reference to the tool support. In certain embodiments, the surgical instrument is a drill bit, tap, screw driver, or an awl. For example, the surgical instrument may be a drill bit and the surgical instrument guide may be a drill guide. In certain embodiments, the surgical instrument guide is configured to be used to guide a screw implant and a tissue protector.

The disclosed technology, in certain embodiments, includes a robotic arm with an end effector comprising a surgical instrument guide configured to hold and/or restrict movement of a surgical instrument therethrough. The system may include a manipulator configured to allow robotically-assisted or unassisted positioning and/or movement of the surgical instrument guide by a user with at least four degrees of freedom to align an axis defined by the instrument guide at a desired trajectory (e.g., a desired path of the surgical tool) in relation to a patient situation. The surgical instrument guide may include a rigid hollow tubular structure having a first open end and a second open end and the structure may define the axis along which movement of a surgical instrument (fitted with a tool support) sliding through the structure is restricted.

The disclosed technology, in certain embodiments, includes a method of performing surgery with a robotic surgical system. The method may include moving a mobile cart transporting a robotic surgical system comprising a robotic arm in proximity to an operating table, wherein the robotic arm has an end effector comprising a surgical instrument guide attached thereto, the surgical instrument guide configured to hold and/or restrict movement of a surgical instrument therethrough. The method may include stabilizing the mobile cart and maneuvering the robotic arm to a desired position to align an axis defined by the instrument guide at a desired trajectory in relation to a patient situation. The surgical instrument guide may include a rigid hollow tubular structure having a first open end and a second open end, said structure defining the axis along which movement of a surgical instrument (fitted with a tool support) sliding through the structure is restricted.

Stabilizing the mobile cart may include extracting one or more rigid legs on the mobile cart such that the mobile cart rests on the one or more rigid legs of the mobile cart. In certain embodiments, stabilizing the mobile cart includes retracting one or more wheels on the mobile cart such that the mobile cart rests on one or more rigid legs of the mobile cart.

In certain embodiments, the method includes fixing the position of the robotic arm (and, therefore, the position of the surgical instrument guide) and maneuvering the surgical instrument in a manner that is constrained by the surgical instrument guide. In certain embodiments, prior to maneuvering the robotic arm to a desired position, obtaining or accessing a CT scan, 3D CT scan, fluoroscopy, 3D fluoroscopy, or natural landmark-based image of the patient situation. The method may include maneuvering the surgical instrument through the surgical instrument guide and maneuvering the drill bit through the drill bit guide.

The disclosed technology, in certain embodiments, includes a surgical instrument guide for use with a robotic surgical system. The surgical instrument guide may include a rigid hollow tubular structure having a first open end and a second open end, said structure defining an axis along which movement of a surgical instrument (fitted with a tool support) sliding through the structure is restricted. The tubular structure may have an interior surface shaped and sized to accommodate the tool support sliding through the guide such that movement of the tool support is constrained in all directions except along the axis defined by the guide. The tubular structure may have an exterior surface comprising at least one flange that is configured for secure coupling of the guide to an end effector of the robotic surgical system. The tubular structure, in some implementations, includes a longitudinal notch along its length, wherein the longitudinal notch is sized in relation to a peg to (i) permit a navigation marker attached to the tool support via the peg to be viewable by a navigation camera along an entire range of movement of the tool support through the guide, (ii) constrain movement of the marker in a fixed orientation along the axis defined by the guide, and (ii) permit the tool support to slide along the axis defined by the guide while the guide is held in a fixed position by the robotic surgical system.

In certain embodiments, the surgical instrument guide includes a lock that, when engaged, restricts (e.g., prevents) movement of the surgical instrument within the rigid hollow tubular structure. The lock, in some implementations, when engaged, prevents movement of the surgical instrument within the rigid hollow tubular structure beyond a preset position along the axis defined by the guide. The lock, when engaged, may prevent removal of the surgical instrument from the surgical instrument guide. The lock may be an end lock that, when engaged, prevents removal of the surgical instrument from the surgical instrument guide. The lock may be an intermediate lock that, when engaged, prevents movement of the surgical instrument within the rigid hollow tubular structure beyond a preset position along the axis defined by the guide.

In certain embodiments, the surgical instrument guide includes an instrument position sensor (e.g., inductive sensor, capacitive sensor, resistive sensor, mechanical end switches, optical measuring device, force sensing device, or other similar position sensor) configured to detect the position of the surgical instrument in the rigid hollow tubular structure.

The disclosed technology, in certain embodiments, includes a robotic surgical system for performing surgery. The system may include a robotic arm with an end effector comprising a surgical instrument guide configured to hold and/or restrict movement of a surgical instrument therethrough, and a manipulator configured to allow robotically-assisted or unassisted positioning and/or movement of the surgical instrument guide by a user with at least four degrees of freedom to align an axis defined by the instrument guide at a desired trajectory in relation to a patient situation. The surgical instrument guide may include a rigid hollow tubular structure having a first open end and a second open end, said structure defining the axis along which movement of a surgical instrument (fitted with a tool support) sliding through the structure is restricted. The tubular structure has an interior surface shaped and sized to accommodate the tool support sliding through the guide such that movement of the tool support is constrained in all directions except along the axis defined by the guide. The tubular structure may have an exterior surface comprising at least one flange that is configured for secure coupling of the guide to the end-effector of the robotic surgical system. The tubular structure may include a longitudinal notch along its length, wherein the longitudinal notch is sized in relation to a peg to (i) permit a navigation marker attached to the tool support via the peg to be viewable by a navigation camera along an entire range of movement of the tool support through the guide, (ii) constrain movement of the marker in a fixed orientation along the axis defined by the guide, and (ii) permit the tool support to slide along the axis defined by the guide while the guide is held in a fixed position by the robotic surgical system. The surgical instrument guide may include a lock that, when engaged, restricts (e.g., prevents) movement of the surgical instrument within the rigid hollow tubular structure.

The disclosed technology, in certain embodiments, includes a method of performing surgery with a robotic surgical system. The method may include obtaining access to one or more vertebrae of a patient; attaching a patient navigation marker to the patient; registering the patient (e.g., using intra-operative images of the patient situation; e.g., 3D fluoroscopy images); moving a mobile cart transporting a robotic surgical system that includes a robotic arm in proximity to an operating table, wherein the robotic arm has an end effector that includes a surgical instrument guide attached thereto, the surgical instrument guide configured to hold and/or restrict movement of a surgical instrument therethrough; stabilizing the mobile cart; inserting a first surgical instrument into the surgical instrument guide until an intermediate lock of the surgical instrument guide is engaged; maneuvering the robotic arm to a desired position to align an axis defined by the instrument guide at a desired trajectory in relation to a patient situation, wherein the surgical instrument guide includes a rigid hollow tubular structure having a first open end and a second open end, said structure defining the axis along which movement of a surgical instrument (fitted with a tool support) sliding through the structure is restricted; fixing the position of the robotic arm (and, therefore, the position of the surgical instrument guide); maneuvering the surgical instrument along the desired trajectory, wherein the robotic surgical system assists in said maneuvering; releasing, the intermediate lock and placing the robotic arm in a hold position mode; manually preparing a hole for a screw using the first surgical instrument; removing the first surgical instrument from the surgical instrument guide; and inserting an implant through the guiding tube and fixing the implant to one of the one or more vertebrae.

The disclosed technology, in certain embodiments, includes a method of performing surgery with a robotic surgical system. The method may include attaching a patient navigation marker to the patient; registering the patient (e.g., using intra-operative images of the patient situation. e.g., 3D fluoroscopy images); moving a mobile cart transporting a robotic surgical system that includes a robotic arm in proximity to an operating table, wherein the robotic arm has an end effector that includes a surgical instrument guide attached thereto, the surgical instrument guide configured to hold and/or restrict movement of a surgical instrument therethrough; stabilizing the mobile cart; inserting a first surgical instrument into the surgical instrument guide until an intermediate lock of the surgical instrument guide is engaged; maneuvering the robotic arm to a desired position to align an axis defined by the instrument guide at a desired trajectory in relation to a patient situation, wherein the surgical instrument guide includes a rigid hollow tubular structure having a first open end and a second open end, said structure defining the axis along which movement of a surgical instrument (fitted with a tool support) sliding through the structure is restricted, wherein the desired trajectory is stored in a memory device of the robotic surgical system; maneuvering the robotic arm such that a surgeon may manually access one or more vertebrae; obtaining access to one or more vertebrae of a patient; maneuvering the robotic arm such to the desired position to align the axis defined by the instrument guide at the desired trajectory, wherein the robotic surgical system assists in said maneuvering; maneuvering the surgical instrument along the desired trajectory, wherein the robotic surgical system assists in said maneuvering; releasing, the intermediate lock and placing the robotic arm in a hold position mode; manually preparing a hole for a screw using the first surgical instrument; removing the first surgical instrument from the surgical instrument guide; and inserting an implant through the guiding tube and fixing the implant to one of the one or more vertebrae.

The disclosed technology, in certain embodiments, A surgical instrument guide for use with a robotic surgical system, the surgical instrument guide comprising a rigid hollow tubular structure having a first open end and a second open end, said structure defining an axis along which movement of a surgical instrument (fitted with a tool support) sliding through the structure is restricted, wherein the tubular structure has an interior surface shaped and sized to accommodate the tool support sliding through the guide such that movement of the tool support is constrained in all directions except along the axis defined by the guide, wherein the tubular structure has an exterior surface comprising at least one flange that is configured for secure coupling of the guide to an end effector of the robotic surgical system, and wherein the tubular structure comprises a longitudinal notch along its length, wherein the longitudinal notch is sized in relation to a peg to (i) permit a navigation marker attached to the tool support via the peg to be viewable by a navigation camera along an entire range of movement of the tool support through the guide, (ii) constrain movement of the marker in a fixed orientation along the axis defined by the guide, and (ii) permit the tool support to slide along the axis defined by the guide while the guide is held in a fixed position by the robotic surgical system.

The disclosed technology, in certain embodiments, includes a robotic surgical system for performing surgery. In some implementations, the system includes: a robotic arm with an end effector comprising a surgical instrument guide configured to hold and/or restrict movement of a surgical instrument therethrough; and a manipulator configured to allow robotically-assisted or unassisted positioning and/or movement of the surgical instrument guide by a user with at least four degrees of freedom to align an axis defined by the instrument guide at a desired trajectory in relation to a patient situation, wherein the surgical instrument guide comprises a rigid hollow tubular structure having a first open end and a second open end, said structure defining the axis along which movement of a surgical instrument (fitted with a tool support) sliding through the structure is restricted, wherein the tubular structure has an interior surface shaped and sized to accommodate the tool support sliding through the guide such that movement of the tool support is constrained in all directions except along the axis defined by the guide, wherein the tubular structure has an exterior surface comprising at least one flange that is configured for secure coupling of the guide to the end-effector of the robotic surgical system, and wherein the tubular structure comprises a longitudinal notch along its length, wherein the longitudinal notch is sized in relation to a peg to (i) permit a navigation marker attached to the tool support via the peg to be viewable by a navigation camera along an entire range of movement of the tool support through the guide, (ii) constrain movement of the marker in a fixed orientation along the axis defined by the guide, and (ii) permit the tool support to slide along the axis defined by the guide while the guide is held in a fixed position by the robotic surgical system.

In certain embodiments, the surgical instrument is a drill bit, tap, screw driver, or awl. In certain embodiments, the surgical instrument is a drill bit and the surgical instrument guide is a drill guide. In certain embodiments, the robotic surgical system is for use in spinal surgery.

In certain embodiments, the rigid hollow tubular structure is a cylindrical structure. In certain embodiments, the longitudinal notch is a slot. In certain embodiments, the longitudinal notch is sized in relation to a peg to permit the surgical instrument to slide along the axis of insertion in reference to the tool support. In certain embodiments, the navigation marker is used by navigation camera to track the surgical instrument. In certain embodiments, the surgical instrument guide is configured to be used to guide a screw implant and a tissue protector.

In certain embodiments, the manipulator is attached to the robotic arm. In certain embodiments, the manipulator is molded into the robotic arm. In certain embodiments, the axis can be aligned with the desired trajectory in relation to the patient situation via the manipulator.

The disclosed technology, in certain embodiments, includes a method of performing surgery with a robotic surgical system. In certain embodiments, the method includes: moving a mobile cart transporting a robotic surgical system comprising a robotic arm in proximity to an operating table, wherein the robotic arm has an end effector comprising a surgical instrument guide attached thereto, the surgical instrument guide configured to hold and/or restrict movement of a surgical instrument therethrough; stabilizing the mobile cart; maneuvering the robotic arm to a desired position to align an axis defined by the instrument guide at a desired trajectory in relation to a patient situation, wherein the surgical instrument guide comprises a rigid hollow tubular structure having a first open end and a second open end, said structure defining the axis along which movement of a surgical instrument (fitted with a tool support) sliding through the structure is restricted; fixing the position of the robotic arm (and, therefore, the position of the surgical instrument guide); and maneuvering the surgical instrument in a manner that is constrained by the surgical instrument guide, wherein: the surgical instrument is fitted with a tool support shaped and sized to slide through the surgical instrument guide along the axis defined by the guide, the tubular structure of the surgical instrument guide has an interior surface shaped and sized to accommodate the tool support sliding through the guide such that movement of the tool support is constrained in all directions except along the axis defined by the guide, and the tubular structure comprises a longitudinal notch along its length, wherein the longitudinal notch is sized in relation to a peg to (i) permit a marker attached to the tool support via the peg to be viewable by a navigation camera along an entire range of movement of the tool support through the guide, (ii) constrain movement of the navigation marker in a fixed orientation along the axis defined by the guide, and (ii) permit the tool support to slide along the axis defined by the guide while the guide is held in a fixed position by the robotic surgical system.

In certain embodiments, stabilizing the mobile cart includes extracting one or more rigid legs on the mobile cart such that the mobile cart rests on the one or more rigid legs of the mobile cart. In certain embodiments, stabilizing the mobile cart includes retracting one or more wheels on the mobile cart such that the mobile cart rests on one or more rigid legs of the mobile cart.

In certain embodiments, prior to maneuvering the robotic arm to a desired position, the method includes obtaining or accessing a CT scan, 3D CT scan, fluoroscopy, 3D fluoroscopy, or natural landmark-based image of the patient situation. In certain embodiments, the method includes maneuvering the surgical instrument through the surgical instrument guide. In certain embodiments, the method includes maneuvering the drill bit through the drill bit guide.

In certain embodiments, the desired trajectory is a desired path of the surgical tool. In certain embodiments, the tubular structure includes a second longitudinal notch along its length, wherein the second longitudinal notch is sized in relation to a peg to (i) permit a navigation marker attached to the tool support via the peg to be viewable by a navigation camera along an entire range of movement of the tool support through the guide, (ii) constrain movement of the marker in a fixed orientation along the axis defined by the guide, and (ii) permit the tool support to slide along the axis defined by the guide while the guide is held in a fixed position by the robotic surgical system.

The disclosed technology, in certain embodiments, includes a surgical instrument guide for use with a robotic surgical system. In certain embodiments, the surgical instrument guide includes a rigid hollow tubular structure having a first open end and a second open end, said structure defining an axis along which movement of a surgical instrument (fitted with a tool support) sliding through the structure is restricted, wherein the tubular structure has an interior surface shaped and sized to accommodate the tool support sliding through the guide such that movement of the tool support is constrained in all directions except along the axis defined by the guide, wherein the tubular structure has an exterior surface comprising at least one flange that is configured for secure coupling of the guide to an end effector of the robotic surgical system, and wherein the tubular structure comprises a longitudinal notch along its length, wherein the longitudinal notch is sized in relation to a peg to (i) permit a navigation marker attached to the tool support via the peg to be viewable by a navigation camera along an entire range of movement of the tool support through the guide, (ii) constrain movement of the marker in a fixed orientation along the axis defined by the guide, and (ii) permit the tool support to slide along the axis defined by the guide while the guide is held in a fixed position by the robotic surgical system; and a lock that, when engaged, restricts (e.g., prevents) movement of the surgical instrument within the rigid hollow tubular structure.

In certain embodiments, the lock, when engaged, prevents movement of the surgical instrument within the rigid hollow tubular structure beyond a preset position along the axis defined by the guide. In certain embodiments, the lock, when engaged, prevents removal of the surgical instrument from the surgical instrument guide. In certain embodiments, the lock is an end lock that, when engaged, prevents removal of the surgical instrument from the surgical instrument guide. In certain embodiments, the lock is an intermediate lock that, when engaged, prevents movement of the surgical instrument within the rigid hollow tubular structure beyond a preset position along the axis defined by the guide.

In certain embodiments, the disclosed technology includes an instrument position sensor (e.g., inductive sensor, capacitive sensor, resistive sensor, mechanical end switches, optical measuring device, force sensing device, or other similar position sensor) configured to detect the position of the surgical instrument in the rigid hollow tubular structure.

In certain embodiments, the robotic surgical system includes: a robotic arm with an end effector comprising a surgical instrument guide configured to hold and/or restrict movement of a surgical instrument therethrough; and a manipulator configured to allow robotically-assisted or unassisted positioning and/or movement of the surgical instrument guide by a user with at least four degrees of freedom to align an axis defined by the instrument guide at a desired trajectory in relation to a patient situation, wherein the surgical instrument guide comprises a rigid hollow tubular structure having a first open end and a second open end, said structure defining the axis along which movement of a surgical instrument (fitted with a tool support) sliding through the structure is restricted, wherein the tubular structure has an interior surface shaped and sized to accommodate the tool support sliding through the guide such that movement of the tool support is constrained in all directions except along the axis defined by the guide, wherein the tubular structure has an exterior surface comprising at least one flange that is configured for secure coupling of the guide to the end-effector of the robotic surgical system, wherein the tubular structure comprises a longitudinal notch along its length, wherein the longitudinal notch is sized in relation to a peg to (i) permit a navigation marker attached to the tool support via the peg to be viewable by a navigation camera along an entire range of movement of the tool support through the guide, (ii) constrain movement of the marker in a fixed orientation along the axis defined by the guide, and (ii) permit the tool support to slide along the axis defined by the guide while the guide is held in a fixed position by the robotic surgical system, and wherein the surgical instrument guide comprises a lock that, when engaged, restricts (e.g., prevents) movement of the surgical instrument within the rigid hollow tubular structure.

The disclosed technology, in certain embodiments, includes a method of performing surgery with a robotic surgical system, the method including: obtaining access to one or more vertebrae of a patient; attaching a patient navigation marker to the patient; registering the patient (e.g., using intra-operative images of the patient situation; e.g., 3D fluoroscopy images); moving a mobile cart transporting a robotic surgical system comprising a robotic arm in proximity to an operating table, wherein the robotic arm has an end effector comprising a surgical instrument guide attached thereto, the surgical instrument guide configured to hold and/or restrict movement of a surgical instrument therethrough; stabilizing the mobile cart; inserting a first surgical instrument into the surgical instrument guide until an intermediate lock of the surgical instrument guide is engaged; maneuvering the robotic arm to a desired position to align an axis defined by the instrument guide at a desired trajectory in relation to a patient situation, wherein the surgical instrument guide comprises a rigid hollow tubular structure having a first open end and a second open end, said structure defining the axis along which movement of a surgical instrument (fitted with a tool support) sliding through the structure is restricted; fixing the position of the robotic arm (and, therefore, the position of the surgical instrument guide); maneuvering the surgical instrument along the desired trajectory, wherein the robotic surgical system assists in said maneuvering; releasing, the intermediate lock and placing the robotic arm in a hold position mode; manually preparing a hole for a screw using the first surgical instrument; removing the first surgical instrument from the surgical instrument guide; and inserting an implant through the guiding tube and fixing the implant to one of the one or more vertebrae.

The disclosed technology, in certain embodiments, includes a method of performing surgery with a robotic surgical system, the method includes: attaching a patient navigation marker to the patient; registering the patient (e.g., using intra-operative images of the patient situation. e.g., 3D fluoroscopy images); moving a mobile cart transporting a robotic surgical system comprising a robotic arm in proximity to an operating table, wherein the robotic arm has an end effector comprising a surgical instrument guide attached thereto, the surgical instrument guide configured to hold and/ or restrict movement of a surgical instrument therethrough; stabilizing the mobile cart; inserting a first surgical instrument into the surgical instrument guide until an intermediate lock of the surgical instrument guide is engaged; maneuvering the robotic arm to a desired position to align an axis defined by the instrument guide at a desired trajectory in relation to a patient situation, wherein the surgical instrument guide comprises a rigid hollow tubular structure having a first open end and a second open end, said structure defining the axis along which movement of a surgical instrument (fitted with a tool support) sliding through the structure is restricted, wherein the desired trajectory is stored in a memory device of the robotic surgical system; maneuvering the robotic arm such that a surgeon may manually access one or more vertebrae; obtaining access to one or more vertebrae of a patient; maneuvering the robotic arm such to the desired position to align the axis defined by the instrument guide at the desired trajectory, wherein the robotic surgical system assists in said maneuvering; maneuvering the surgical instrument along the desired trajectory, wherein the robotic surgical system assists in said maneuvering; releasing, the intermediate lock and placing the robotic arm in a hold position mode; manually preparing a hole for a screw using the first surgical instrument; removing the first surgical instrument from the surgical instrument guide; and inserting an implant through the guiding tube and fixing the implant to one of the one or more vertebrae.

In certain embodiments, the surgical instrument is fitted with a tool support shaped and sized to slide through the surgical instrument guide along the axis defined by the guide, the tubular structure of the surgical instrument guide has an interior surface shaped and sized to accommodate the tool support sliding through the guide such that movement of the tool support is constrained in all directions except along the axis defined by the guide, and the tubular structure comprises a longitudinal notch along its length, wherein the longitudinal notch is sized in relation to a peg to (i) permit a marker attached to the tool support via the peg to be viewable by a navigation camera along an entire range of movement of the tool support through the guide, (ii) constrain movement of the navigation marker in a fixed orientation along the axis defined by the guide, and (ii) permit the tool support to slide along the axis defined by the guide while the guide is held in a fixed position by the robotic surgical system.

In certain embodiments, the system includes an instrument position sensor configured to detect the position of the surgical instrument in the rigid hollow tubular structure.

In certain embodiments, the surgical instrument guide includes a lock that, when engaged, restricts (e.g., prevents) movement of the surgical instrument within the rigid hollow tubular structure. In certain embodiments, the surgical instrument guide includes one or more input devices (e.g., one or more electro-mechanical buttons; e.g., two input devices). In certain embodiments, the surgical instrument guide includes an activation switch (e.g., sized and shaped to detect the presence of a surgeon's hand on the surgical instrument guide).

BRIEF DESCRIPTION OF THE FIGURES

The foregoing and other objects, aspects, features, and advantages of the present disclosure will become more apparent and better understood by referring to the following description taken in conjunction with the accompanying drawings, in which:

FIG. 10C is an illustration of an example surgical instrument guide with an end lock for use with a robotic surgical system;

FIG. 11 is an illustration of an example surgical instrument guide for use with a robotic surgical system;

Figure 1:
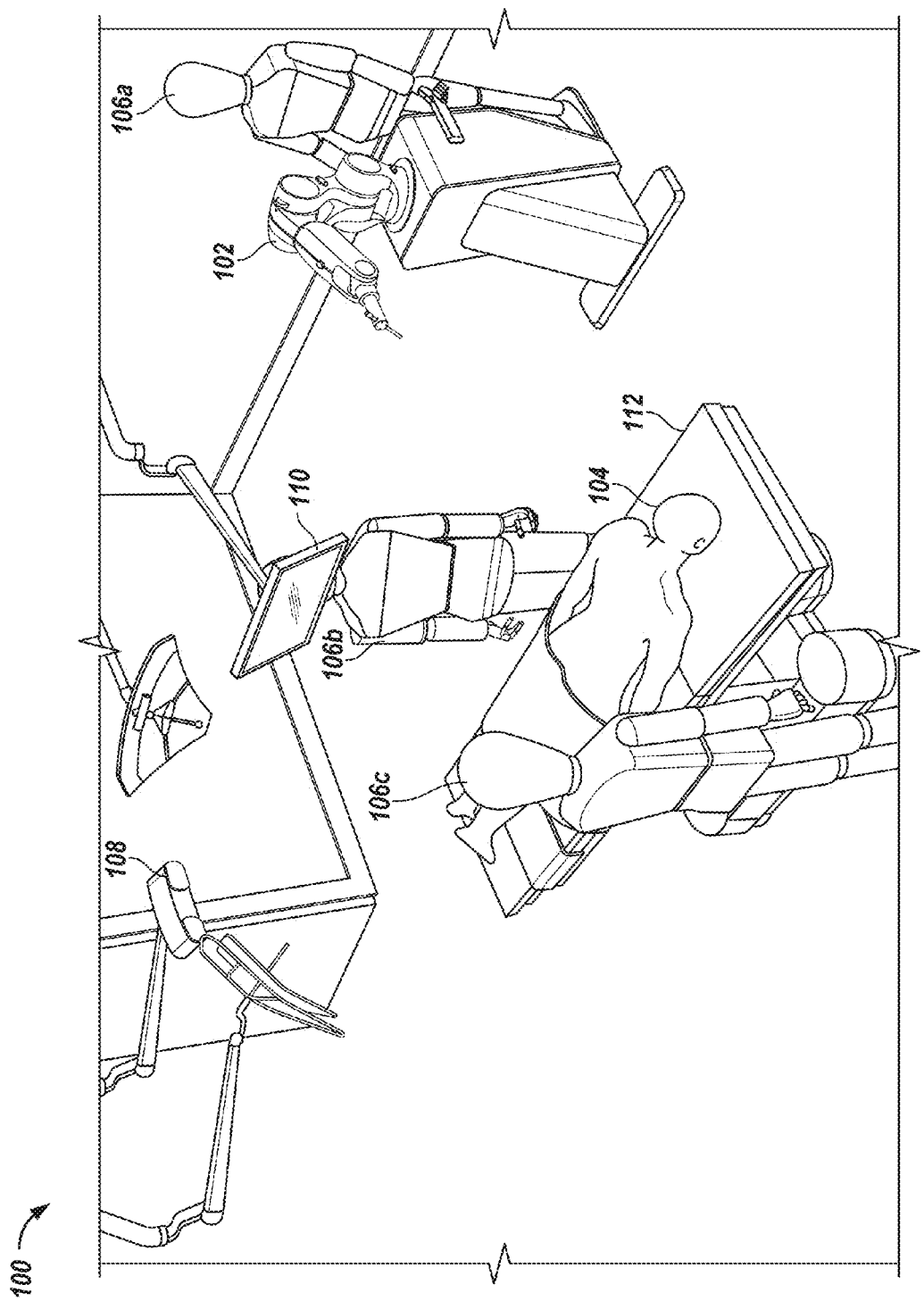
FIG. 1 is an illustration of an example robotic surgical system in an operating room.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

FIG. 1 illustrates an example robotic surgical system in an operating room 100. In some implementations, one or more surgeons, surgical assistants, surgical technologists and/or other technicians (e.g., 106a-c) perform an operation on a patient 104 using a robotic-assisted surgical system. In the operating room 100 the surgeon may be guided by the robotic system to accurately execute an operation. This may be achieved by robotic guidance of the surgical tools, including ensuring the proper trajectory of the tool (e.g., drill or screw). In some implementations, the surgeon defines the trajectory intra-operatively with little or no pre-operative planning. The system allows a surgeon to physically manipulate the tool holder to safely achieve proper alignment of the tool for performing crucial steps of the surgical procedure. Operation of the robot arm by the surgeon (or other operator) in force control mode permits movement of the tool in a measured, even manner that disregards accidental, minor movements of the surgeon. The surgeon moves the tool holder to achieve proper trajectory of the tool (e.g., a drill or screw) prior to operation or insertion of the tool into the patient 104. Once the robotic arm is in the desired position, the arm is fixed to maintain the desired trajectory. The tool holder serves as a stable, secure guide through which a tool may be moved through or slid at an accurate angle. Thus, the disclosed technology provides the surgeon with reliable instruments and techniques to successfully perform his/her surgery.

In some embodiments, the operation may be spinal surgery, such as a discectomy, a foraminotomy, a laminectomy, or a spinal fusion. In some implementations, the surgical robotic system includes a surgical robot 102 on a mobile cart 114. The surgical robot 102 in the example shown in FIG. 1 is positioned in proximity to an operating table 112 without being attached to the operating table 112, thereby providing maximum operating area and mobility to surgeons around the operating table 112 and reducing clutter on the operating table 112. In alternative embodiments, the surgical robot 102 (or cart) is securable to the operating table 112. In certain embodiments, both the operating table 112 and the cart 114 are secured to a common base to prevent any movement of the cart or table 112 in relation to each other, even in the event of an earth tremor.

The mobile cart 114 may permit a user (operator) 106a, such as a technician, nurse, surgeon, or any other medical personnel in the operating room 100, to move the surgical robot 102 to different locations before, during, and/or after a surgical procedure. The mobile cart 104 enables the surgical robot 102 to be easily transported into and out of the operating room 100. For example, a user 106a may move the surgical robot 102 into the operating room 100 from a storage location. In some implementations, the mobile cart 114 may include wheels, a track system, such as a continuous track propulsion system, or other similar mobility systems for translocation of the cart. The mobile cart 114 may include an attached or embedded handle for locomotion of the mobile cart 114 by an operator (e.g., user 106a).

For safety reasons, the mobile cart 114 may be provided with a stabilization system that may be used during a surgical procedure performed with a surgical robot 102. The stabilization mechanism increases the global stiffness of the mobile cart 114 relative to the floor in order to ensure the accuracy of the surgical procedure. In some implementations, the wheels include a locking mechanism that prevents the cart 114 from moving. The stabilizing, braking, and/or locking mechanism may be activated when the machine is turned on. In some implementations, the mobile cart 114 includes multiple stabilizing, braking, and/or locking mechanisms. In some implementations, the stabilizing mechanism is electro-mechanical with electronic activation. The stabilizing, braking, and/or locking mechanism(s) may be entirely mechanical. The stabilizing, braking, and/or locking mechanism(s) may be electronically activated and deactivated.

In some implementations, the surgical robot 102 includes a robotic arm mounted on a mobile cart 114. An actuator may move the robotic arm. The robotic arm may include a force control end-effector configured to hold a surgical tool. The robot 102 may be configured to control and/or allow positioning and/or movement of the end-effector with at least four degrees of freedom (e.g., six degrees of freedom, three translations and three rotations).

In some implementations, the robotic arm is configured to releasably hold a surgical tool, allowing the surgical tool to be removed and replaced with a second surgical tool. The system may allow the surgical tools to be swapped without re-registration, or with automatic or semi-automatic re-registration of the position of the end-effector.

In some implementations, the surgical system includes a surgical robot 102, a tracking detector 108 that captures the position of the patient and different components of the surgical robot 102, and a display screen 110 that displays, for example, real time patient data and/or real time surgical robot trajectories.

In some implementations, a tracking detector 108 monitors the location of patient 104 and the surgical robot 102. The tracking detector 108 may be a camera, a video camera, an infrared detector, field generator and sensors for electro-magnetic tracking or any other motion detecting apparatus. In some implementation, based on the patient and robot position, the display screen 110 displays a projected trajectory and/or a proposed trajectory for the robotic arm of robot 102 from its current location to a patient operation site. By continuously monitoring the patient 104 and robotic arm positions, using tracking detector 108, the surgical system can calculate updated trajectories and visually display these trajectories on display screen 110 to inform and guide surgeons and/or technicians in the operating room 100 using the surgical robot. In addition, in certain embodiments, the surgical robot 102 may also change its position and automatically position itself based on trajectories calculated from the real time patient and robotic arm positions captured using the tracking detector 108. For instance, the trajectory of the end-effector can be automatically adjusted in real time to account for movement of the vertebrae and/or other part of the patient 104 during the surgical procedure.

Figure 2:
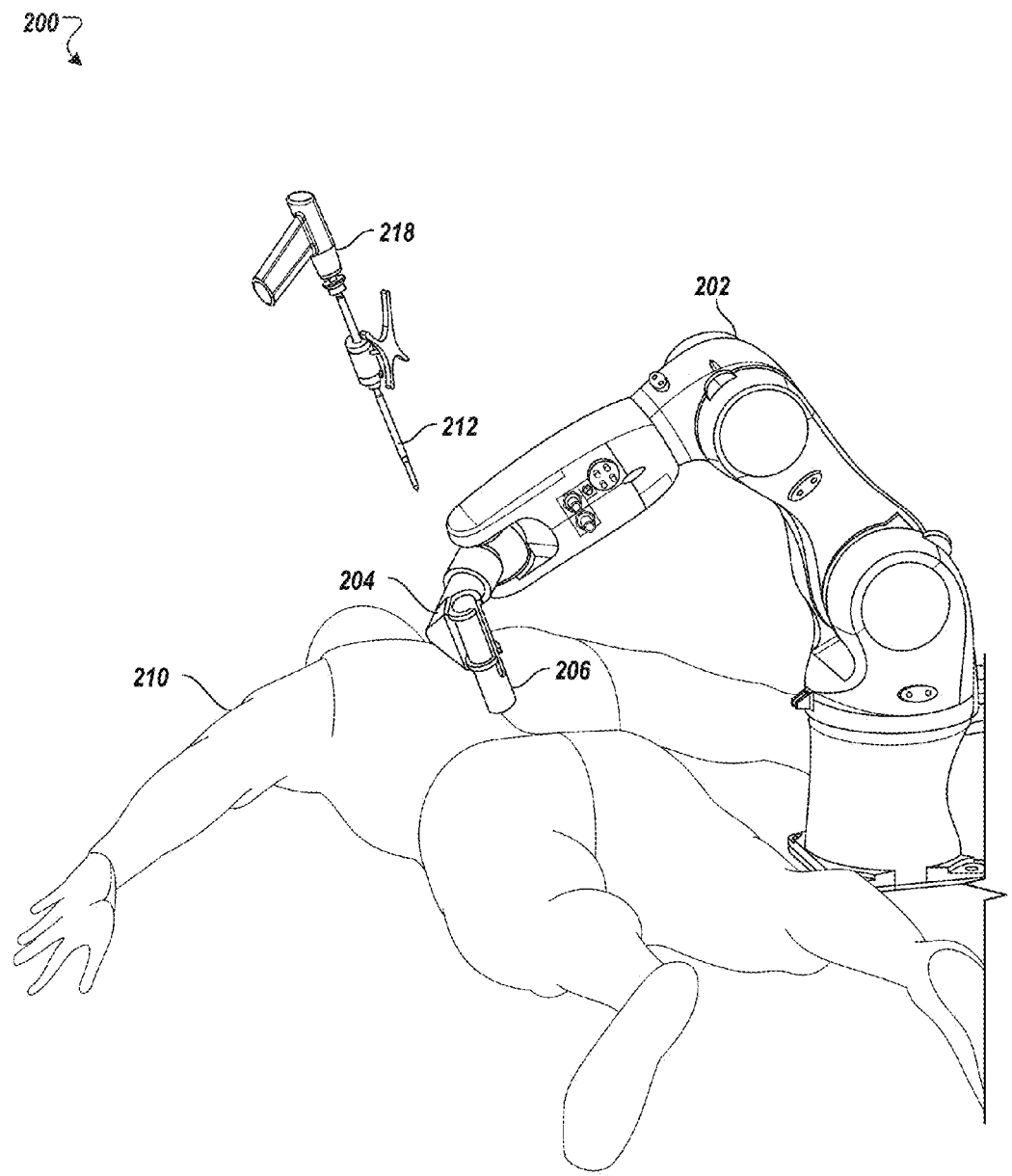
FIG. 2 is an illustration of an example configuration of a robotic arm for performing a surgical operation.

FIG. 2 illustrates an example configuration 200 of a robotic arm 202 for performing a surgical operation. The robotic surgical system includes a robotic arm 202 and a end-effector 204. The manipulator (not shown in FIG. 2), such as a handle on the robotic arm and/or near the end effector, can be used by a surgeon for robotically-assisted or unassisted positioning and/or movement of the surgical instrument guide 206 by a user with at least four degrees of freedom (e.g., six degrees of freedom, three translations and three rotations) to align an axis defined by the instrument guide 206 at a desired trajectory in relation to a patient situation 210. The axis can be aligned with the desired trajectory in relation to the patient situation 210 via the manipulator.

An end-effector, such as surgical instrument guide 206, is coupled to the robotic arm 202 for precisely guiding instruments during surgery. For example, the surgical instrument guide 206 may be coupled to the robotic arm via a flange. The surgical instrument guide 206 is configured to hold and/or restrict movement of a surgical instrument (e.g., drill guide 212) therethrough. As shown in FIG. 2, in some implementations, the surgical instrument is a drill guide 212 through which the drill bit 208 of a drill 218 is passed. Such a system may be used to perform spinal surgery. In some implementations, the surgical tool may be, for example, a tap such as the StealthStation® CR Horizon Legacy Taps from Medtronic, Inc. of Minneapolis, Minn. Other surgical instruments may be used by the system, such as a screw driver or awl. For example, the surgical instrument guide may be configured to be used to guide a screw implant and/or a tissue protector.

Figure 3:
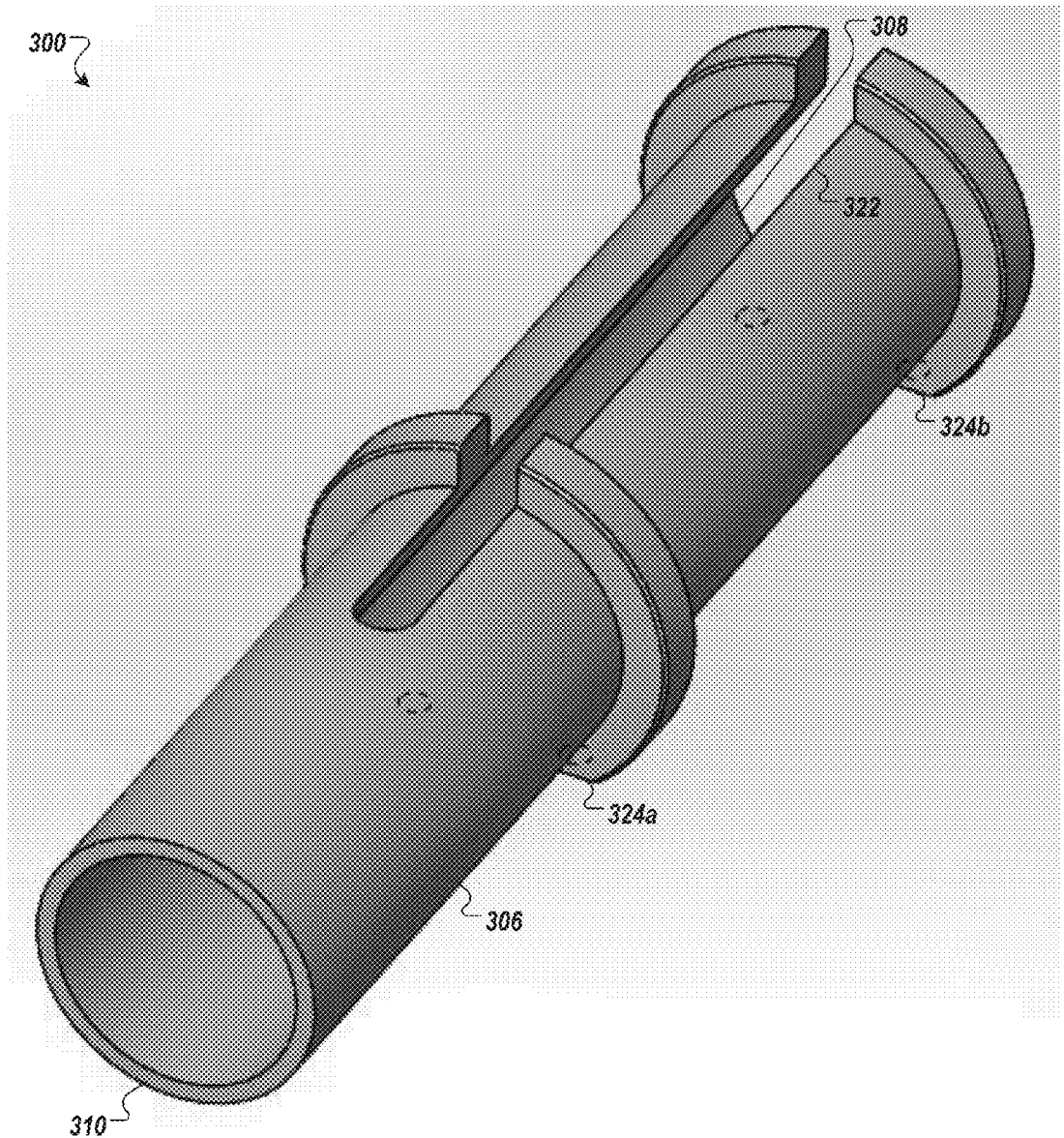
FIG. 3 is an illustration of an example surgical instrument guide for use with a robotic surgical system.

FIG. 3 illustrates an example surgical instrument guide 300 for use with a robotic surgical system. In some implementations, the same guide 300 is used to guide all the instruments utilized with a robotic surgical system. For example, the robot may not move during the complete pedicle preparation and implant placement of one screw. In minimally invasive surgeries, screw extensions may also pass through the guide which prevents the need to move the robot between pedicle preparation and screw placement. This guarantees best possible alignment of screw with respect to previously prepared hole.

In some implementations, the surgical instrument guide comprising a rigid hollow tubular structure 306 having a first open end 308 and a second open end 310. In some implementations, the tubular structure 306 is a cylindrical structure. The tubular structure 306 has one or more flanges 324a-b that are configured for secure coupling of the guide 300 to an end effector of the robotic surgical system. The tubular structure 306, in some implementations, defines an axis along which movement of a surgical instrument (fitted with a tool support) sliding through the structure 306 is restricted. The tubular structure 306 is configured (e.g., an interior surface of the structure 306 is shaped and sized) to permit a tool support to slide through the tubular structure 306 such that movement of the tool support is constrained in all directions except along the axis defined by the tubular structure 306.

Figure 4A:
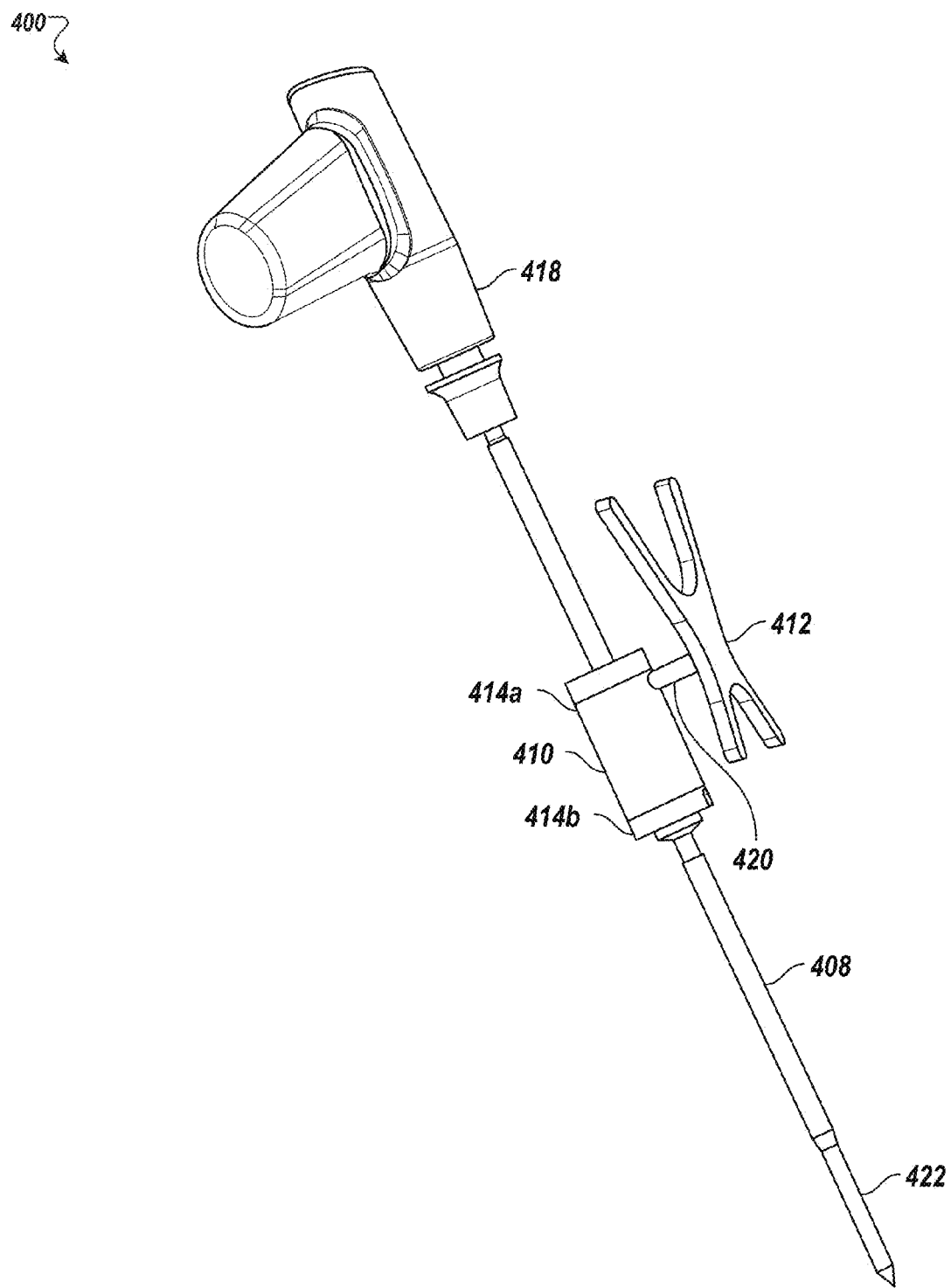
FIGS. 4A-B are illustrations of an example surgical instrument for use with a robotic surgical system.
Figure 4B:
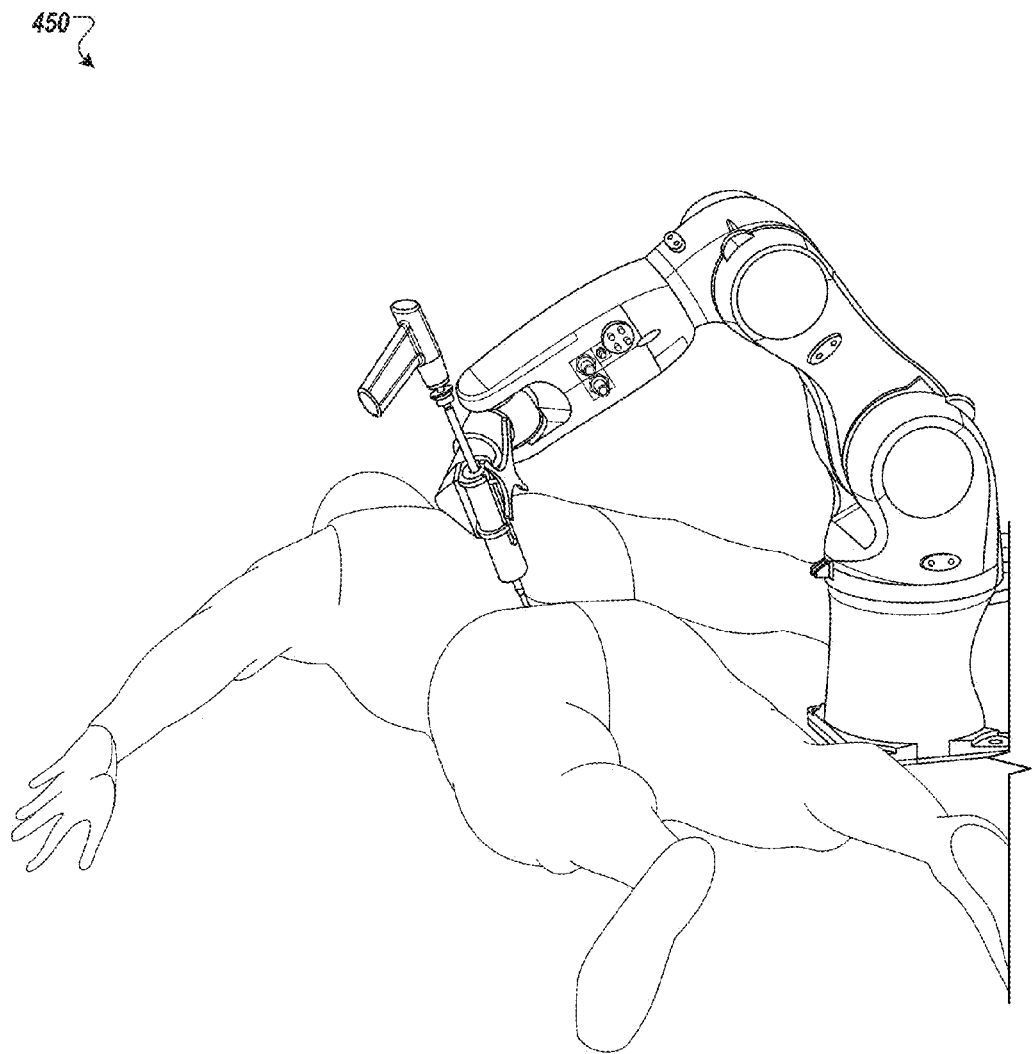

FIGS. 4A-B illustrate an example surgical instrument system 400 for use with the robotic surgical system. As shown in FIG. 4A, the tool support 410 is coupled to an instrument, such as drill bit 408 in this example, that is used with the robotic surgical system. In some implementations, the tool support 410 includes interface bands 414a-b that engage the interior surface of the tubular structure 306 of the guide 300 as shown in FIG. 3. Interface 414a-b slide along the interior surface of the guide and permit the tool support 410 to slide through the guide such that movement of the tool support 410 is constrained in all directions except along the axis defined by the guide. These bands 414a-b are designed in order to slide into the guide allowing the surgeon to achieve a linear motion of the instrument along the guide's axis. The navigation marker 412 is coupled to the tool support 410 via a peg 420. In some implementations, the peg is utilized without the navigation marker to maintain the orientation of the surgical instrument. The navigation marker may be, for example, navigation tracker such as the Dedicated NavLock™ tracker from Medtronic, Inc. of Minneapolis, Minn. In the example illustrated in FIG. 4, the instrument 408 is a drill 418 with a drill bit 422 that passes through a drill guide 408. FIG. 4B illustrates an example surgical operation 450 involving the surgical instrument shown in FIG. 4A and the robotic surgical system disclosed herein.

As shown in FIG. 3, the tubular structure 306, in some implementations, includes a longitudinal notch 322 along its length. In some implementations, the longitudinal notch 322 is a slot. The longitudinal notch 322 is sized in relation to a peg (e.g., peg 420 as shown in FIG. 4) that couples a navigation marker (e.g., 412 as shown in FIG. 4) to a tool support (e.g., 410 as shown in FIG. 4). In some implementations, the peg is utilized without the navigation marker to maintain the orientation of the surgical instrument. As the tool support slides through the guide 300, the notch 322 permits the tool support to slide along the axis defined by the guide while the guide is held in a fixed position by the robotic surgical system. The peg extends through the notch 322 and outside of the guide 300 and permits the navigation marker attached to the tool support via the peg to be viewed by a navigation camera along an entire range of movement of the tool support through the guide 300. In some implementations, the navigation marker is used by navigation camera to track the surgical instrument. The notch 322 may constrain movement of the marker in a fixed orientation along the axis defined by the guide. In some implementations, longitudinal notch 322 is sized in relation to a peg to prevent the surgical instrument from rotating around the axis of insertion in reference to the tool support.

Figure 5A:
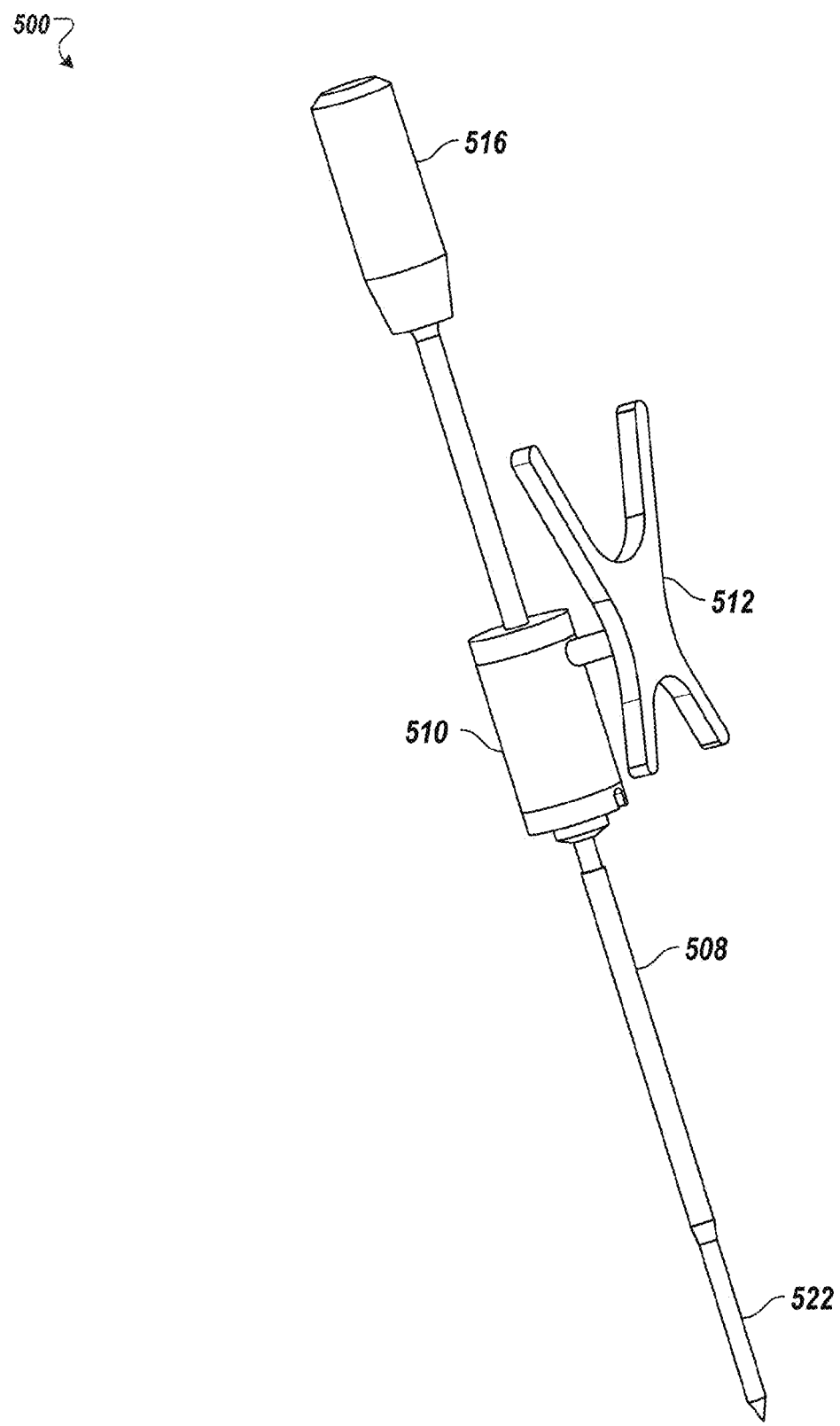
FIGS. 5A-B are illustrations of an example surgical instrument for use with a robotic surgical system.
Figure 5B:
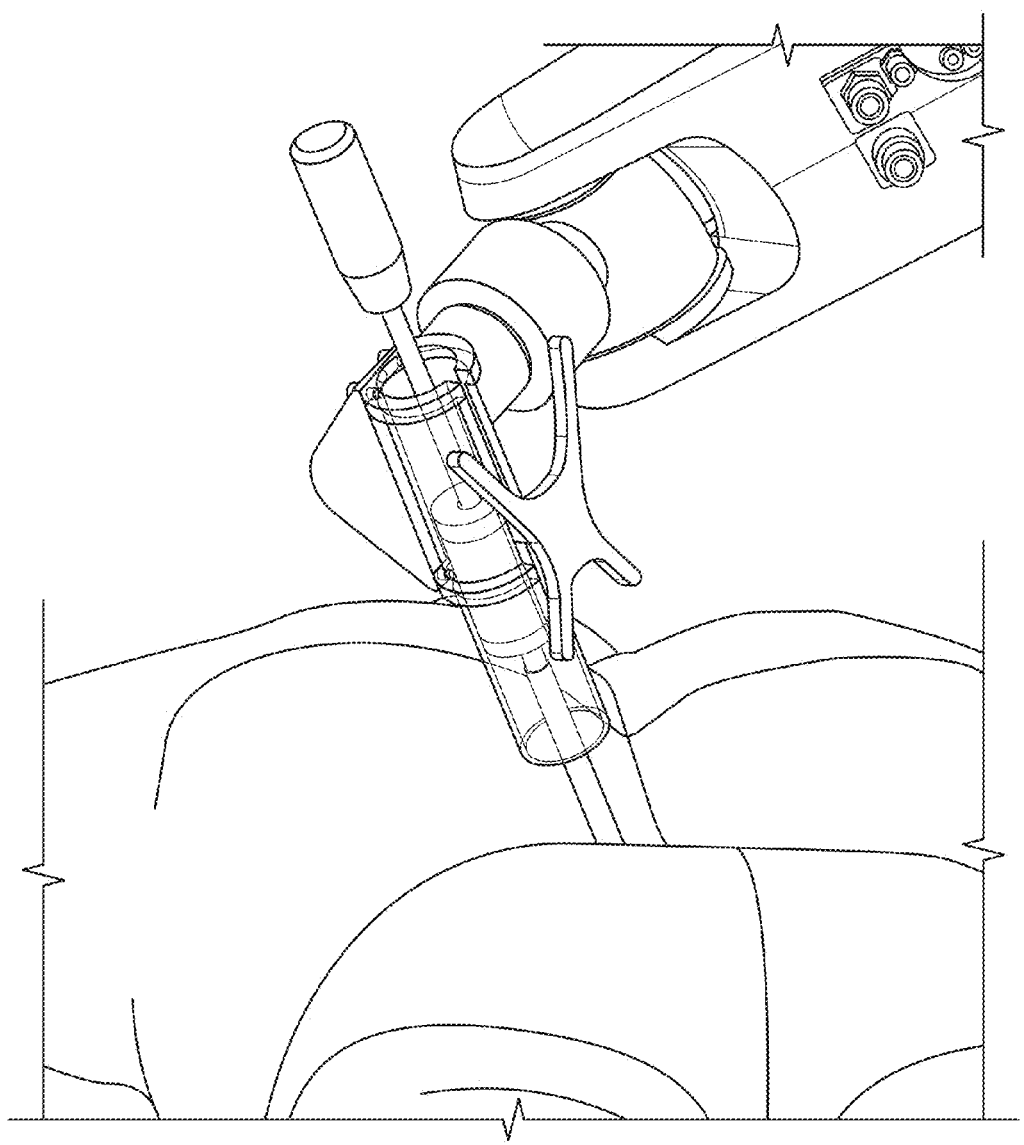

FIGS. 5A-B illustrate an example instrument system 500 for use with the robotic surgical system. The instrument system 500 includes a drill bit 522 that is coupled to a hand drill 516 that may be used by a surgeon during a surgical operation. The instrument system includes a tool support 510 and a navigational marker 512 as described above. The tool support 510 is connected (permanently or removably) to a drill guide 508 through which the drill bit 522 passes. Other surgical instruments may be used with the system, such as a tap, screw driver, or awl. FIG. 5B illustrates an example surgical operation 550 involving the surgical instrument shown in FIG. 5A and the robotic surgical system disclosed herein.

Figure 6:
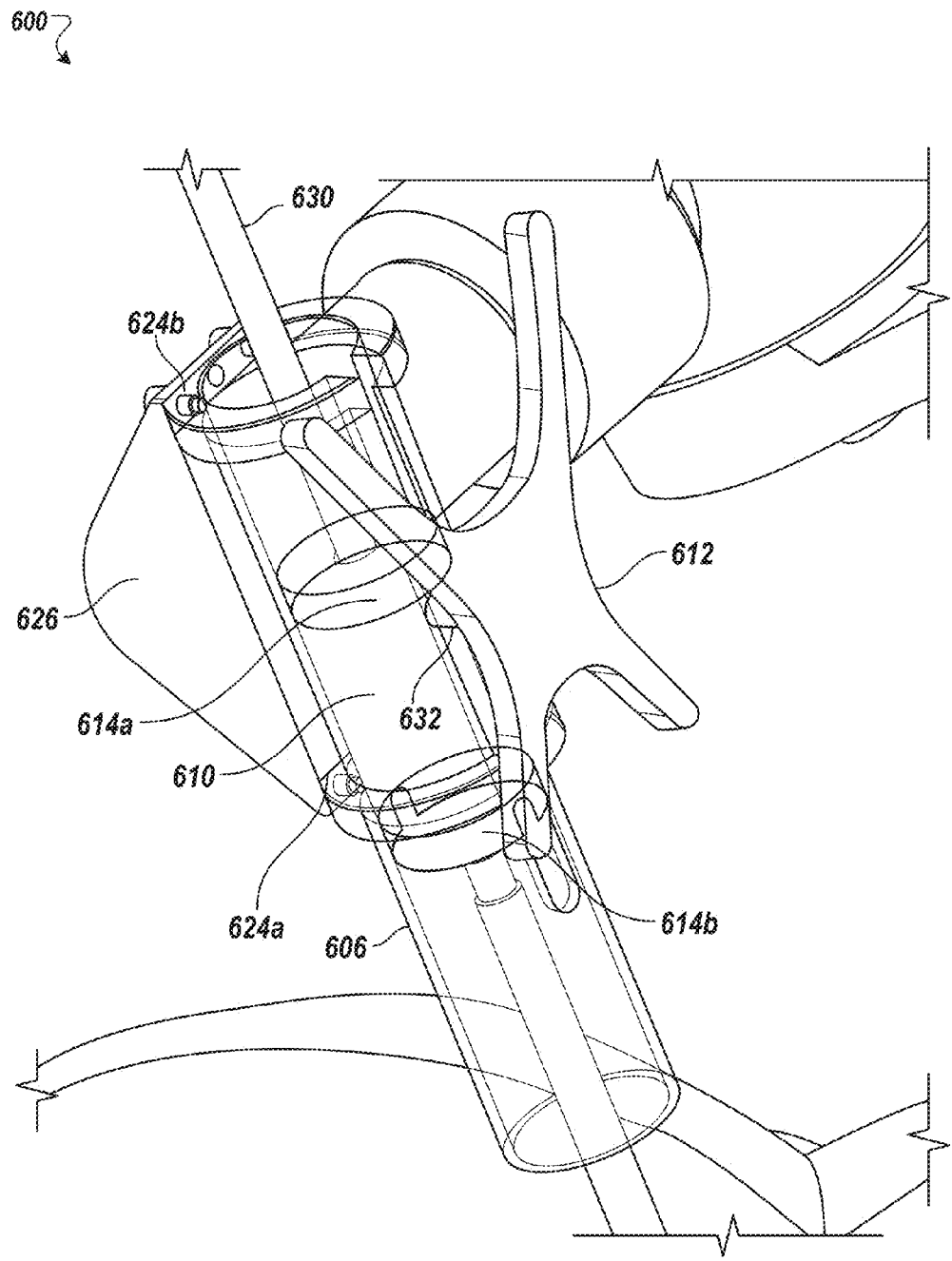
FIG. 6 is an illustration of a surgical instrument being used with a surgical instrument guide.

FIG. 6 is an illustration 600 of a surgical instrument 630 being used with a surgical instrument guide 606. In some implementations, the surgical instrument 630 includes a tool support 610. The tool support 610 includes members 614a-b that engage the interior surface of the guide 606. Members 614a-b slide along the interior surface of the guide 606 and permit the tool support 610 to slide through the guide such that movement of the tool support 610 is constrained in all directions except along the axis defined by the guide. The guide 606, in some implementations, has one or more flanges that are configured for secure coupling of the guide to an end effector of the robotic surgical system. As shown in FIG. 6, the guide 606 has two flanges 624a-b. In this example, the flanges 624a-b are bolted to the manipulator 626. In some implementations, other mounting systems are used. As described above, a navigation marker 612 is coupled to the tool support 610 via a peg 632 such that the navigation marker 612 is viewable by a navigation camera along an entire range of movement of the tool support 610 through the guide 606.

Figure 7A:
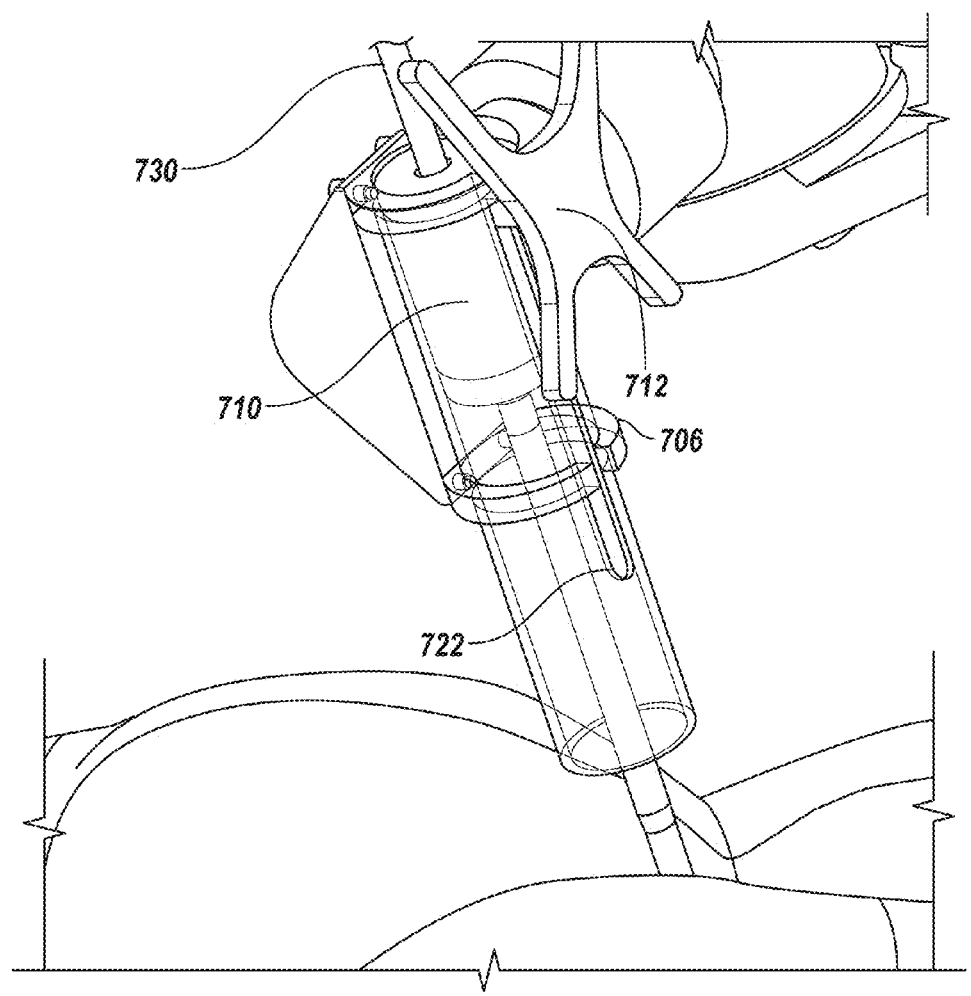
FIGS. 7A-B are illustrations of an example surgical instrument in which a surgical instrument tool is sliding through a surgical instrument guide.
Figure 7B:
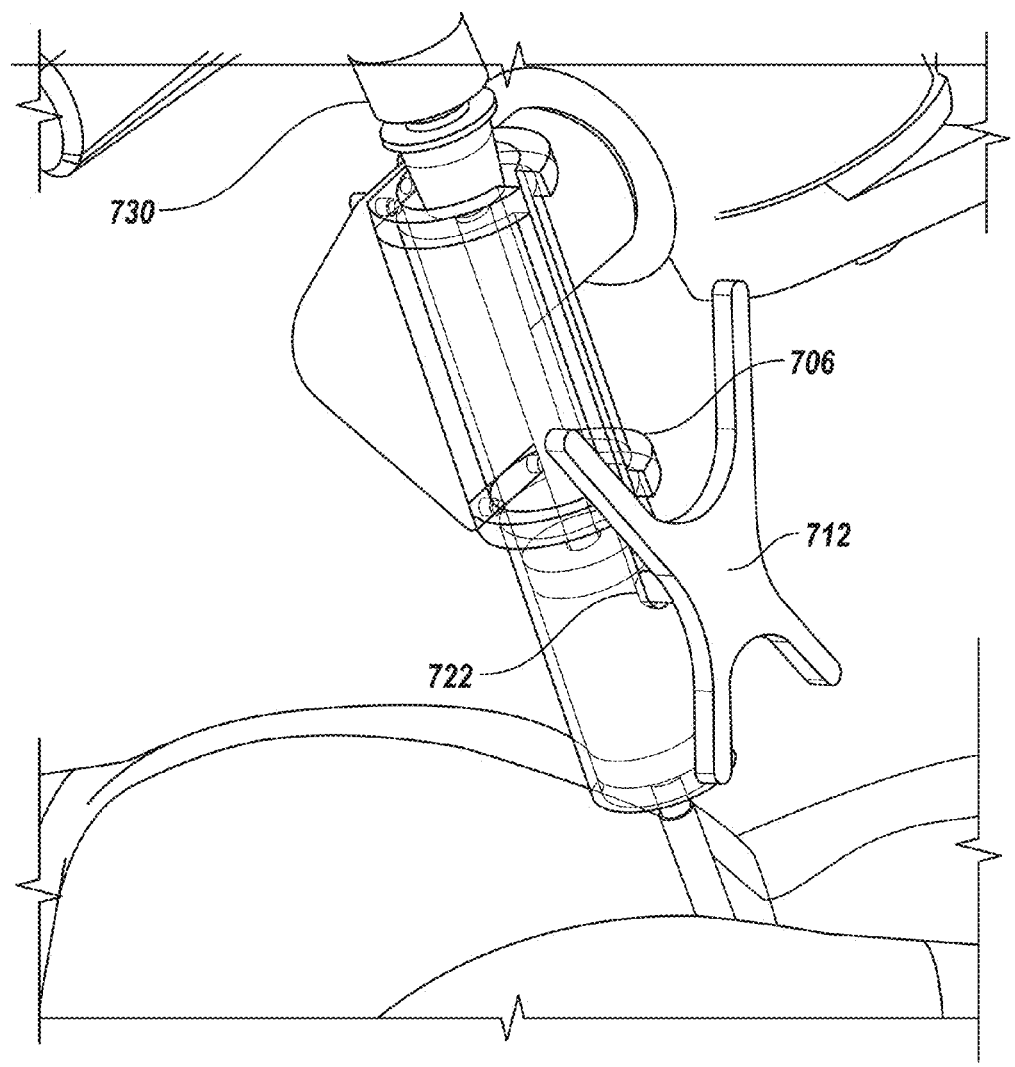

FIGS. 7A-B illustrate an example surgical instrument system 700 in which a surgical instrument 730 slides through a surgical instrument guide 706. As discussed above, the guide 706 includes a notch 722 along its length. As the tool support 710 (described above) slides through the guide 706, the notch 722 permits the tool support to slide along the axis defined by the guide while the guide is held in a fixed position by the robotic surgical system. As the tool support 710 slides through the guide 706 from the position shown in FIG. 7A to the position shown in FIG. 7B, the navigation marker 712 is viewable by a navigation camera along an entire range of movement of the tool support 710 through the guide 706.

Figure 8:
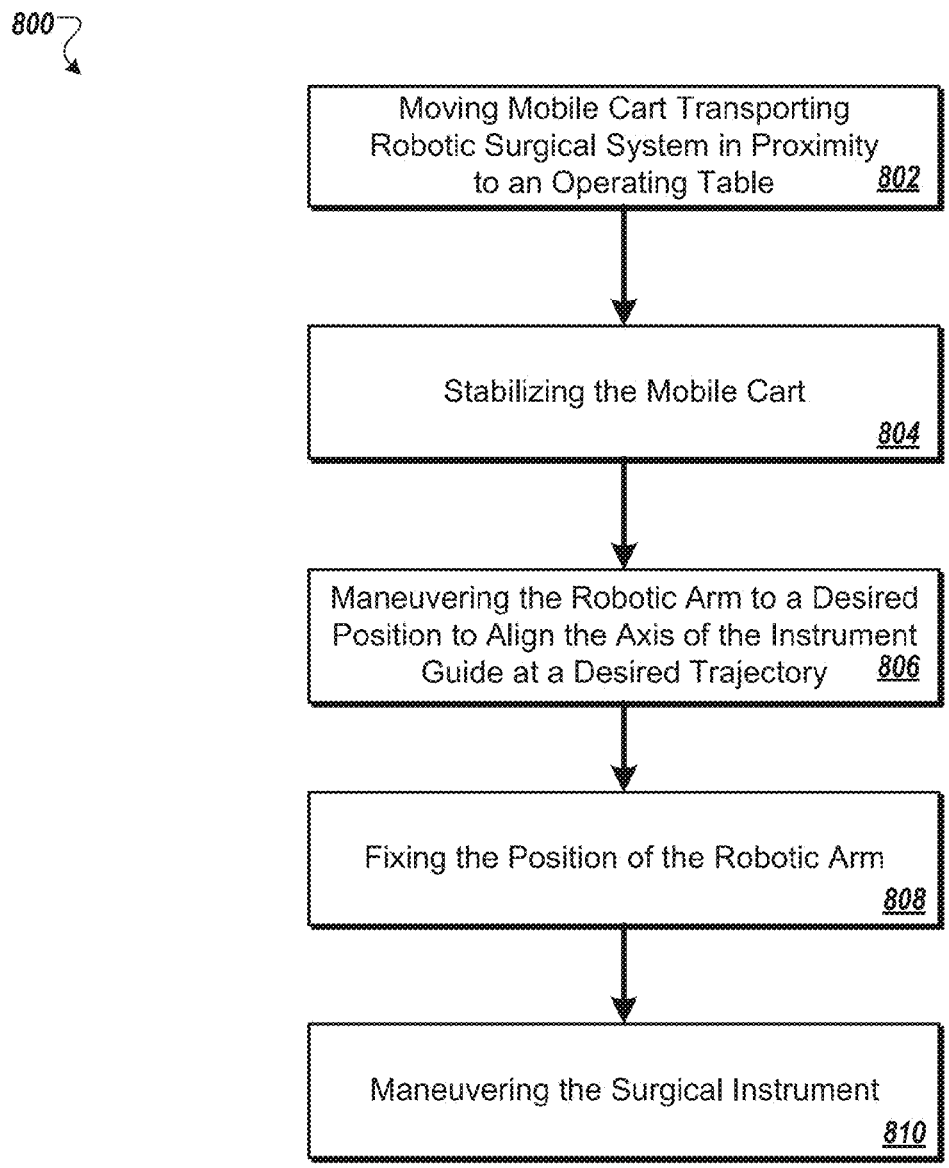
FIG. 8 is a flowchart of an example method of performing surgery with a robotic surgical system.

FIG. 8 is a flowchart of an example method 800 of performing surgery with a robotic surgical system, such as the robotic surgical system disclosed herein. In some implementations, the method 800 includes moving a mobile cart transporting a robotic surgical system comprising a robotic arm in proximity to an operating table (802). As described above, the robotic arm has an end effector comprising a surgical instrument guide attached thereto. The surgical instrument guide is, in some implementations, configured to hold and/or restrict movement of a surgical instrument therethrough.

The method 800 may include stabilizing the mobile cart (804). For safety reasons, the mobile cart is provided with a stabilization system that may be used during a surgical procedure performed with a surgical robot. The stabilization mechanism increases the global stiffness of the mobile cart relative to the floor in order to ensure the accuracy of the surgical procedure. Once stabilization is engaged, the mobile cart is secured in place on the operating room floor and cannot move.

After stabilizing the mobile cart, the robotic arm is maneuvered to a desired position to align an axis defined by the instrument guide at a desired trajectory in relation to a patient situation (806). As described above, the surgical instrument guide may comprise a rigid hollow tubular structure having a first open end and a second open end. The structure may define the axis along which movement of a surgical instrument (fitted with a tool support) sliding through the structure is restricted.

The position of the robotic arm and, therefore, the position of the surgical instrument guide is fixed (808) after the robotic arm is maneuvered to the desired position. After the position of the robotic arm is fixed, a surgical instrument is maneuvered in a manner that is constrained by the surgical instrument guide (810). As described above, the surgical instrument may be fitted with a tool support shaped and sized to slide through the surgical instrument guide along the axis defined by the guide. The tubular structure of the surgical instrument guide may have an interior surface shaped and sized to accommodate the tool support sliding through the guide such that movement of the tool support is constrained in all directions except along the axis defined by the guide. The tubular structure may include a longitudinal notch along its length that is sized in relation to a peg to (i) permit a marker attached to the tool support via the peg to be viewable by a navigation camera along an entire range of movement of the tool support through the guide, (ii) constrain movement of the navigation marker in a fixed orientation along the axis defined by the guide, and (ii) permit the tool support to slide along the axis defined by the guide while the guide is held in a fixed position by the robotic surgical system.

Figure 9:
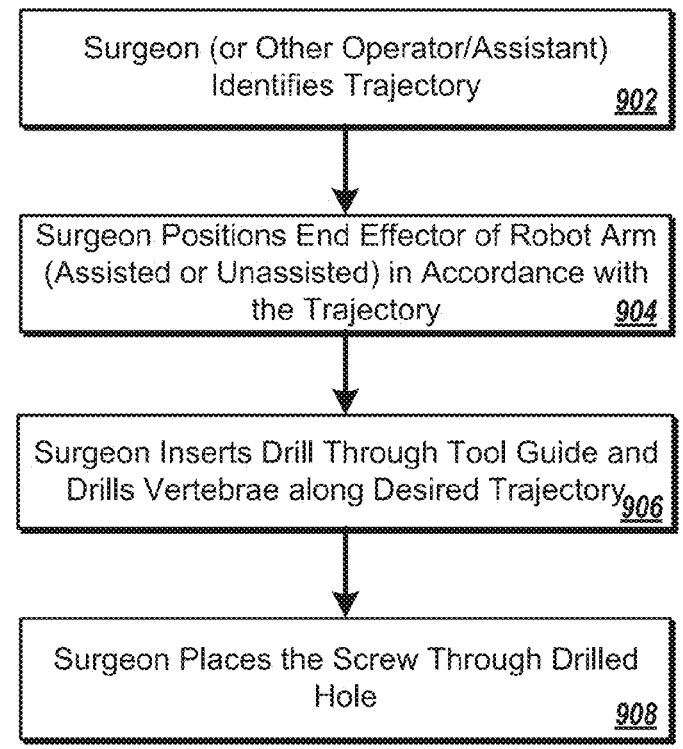
FIG. 9 is a flowchart of an example of a method for performing a minimally invasive surgery using a robotic surgical system as a drill guide.

FIG. 9 is an example of a method 900 for performing a minimally invasive surgery using a robotic surgical system as a drill guide. The surgeon or other operator/assistant identifies a trajectory (902). The trajectory may be identified preoperatively, intraoperatively, or a combination thereof. In some implementations, the trajectory is defined by a computer algorithm. The computer may define the trajectory with or without the surgeon's assistance. In some implementations, the trajectory is presented for the surgeon's approval. Next, the surgeon positions the end effector in accordance with the trajectory (904). The positioning may be assisted or unassisted by the robotic surgical system. In some implementations, the surgeon may be assisted using various types of indications such as visual and/or sound indications. After the position of the robotic arm is fixed, a surgical instrument is maneuvered in a manner that is constrained by the surgical instrument guide. In this example, the surgeon drills through the tool guide (906). In the case in which a drill guide is coupled to the end effector, an operator may insert a drill into the drill guide without moving the position of the end effector or drill guide. Thus, after carefully positioning the drill guide along a desired trajectory, an operator may accurately drill along the desired trajectory.

As described above, the surgical instrument (e.g., the drill) may be fitted with a tool support shaped and sized to slide through the surgical instrument guide along the axis defined by the guide. The tubular structure of the surgical instrument guide may have an interior surface shaped and sized to accommodate the tool support sliding through the guide such that movement of the tool support is constrained in all directions except along the axis defined by the guide. After drilling through the tool guide, the surgeon places the screw through the drilled hole (908).

Figure 10A:
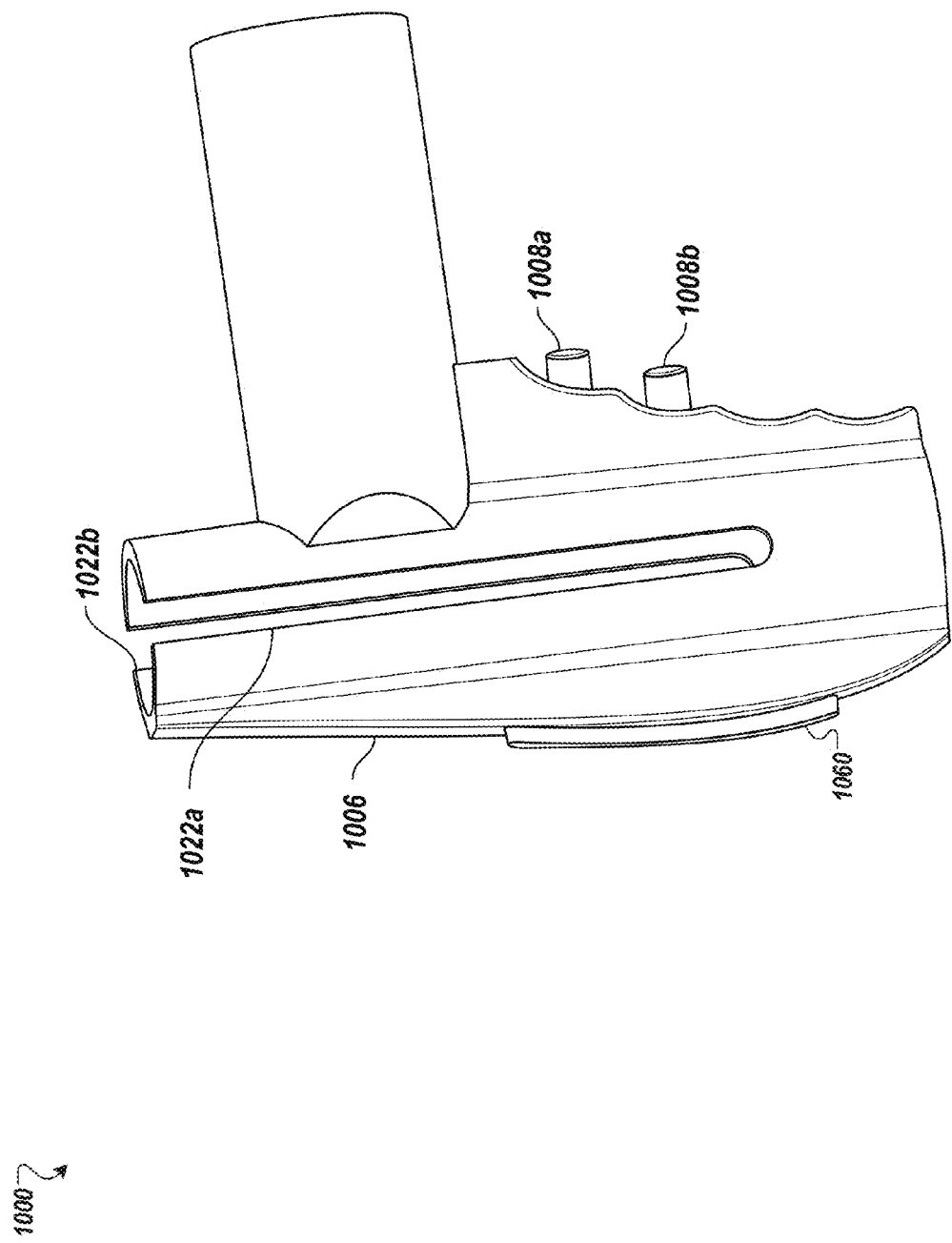
FIG. 10A is an illustration of an example surgical instrument guide for use with a robotic surgical system.

FIG. 10A is an illustration of an example surgical instrument guide for use with a robotic surgical system. In some implementations, the same guide 1000 is used to guide all the instruments utilized with a robotic surgical system. For example, the robot may not move during the complete pedicle preparation and implant placement of one screw. In minimally invasive surgeries, screw extensors may also pass through the guide which prevents the need to move the robot between pedicle preparation and screw placement. In some implementations, this guarantees best possible alignment of screw with respect to previously prepared hole.

In some implementations, the surgical instrument guide comprising a rigid hollow tubular structure 1006 having a first open end and a second open end. In some implementations, the tubular structure 1006 is a cylindrical structure. The tubular structure 1006, in some implementations, defines an axis along which movement of a surgical instrument (fitted with a tool support) sliding through the structure is restricted. The tubular structure 1006 is configured (e.g., an interior surface of the structure 1006 is shaped and sized) to permit a tool support to slide through the guide such that movement of the tool support is constrained in all directions except along the axis defined by the guide.

As shown in FIG. 10A, a guide 1000, in some implementations, includes a tubular structure 1006 (e.g., body), with a first longitudinal notch 1022*a* along its length and a second longitudinal notch 1022*b* along its length. In some implementations, the first notch 1022*a* and second notch 1022*b* are located on opposite sides/portions of the body 1006 of the guide 1000 as shown in FIG. 10A. In some implementations, the guide 1000 includes two or more notches that are spaced evenly (as shown in FIG. 10A) or unevenly around the body of the guide.

In some implementations, the longitudinal notches 1022*a* and 1022*b* are slots. The longitudinal notches 1022*a-b*, in some implementations, are sized in relation to one or more pegs (e.g., peg 420 as shown in FIG. 4) that couples a navigation marker to a tool support. As the tool support slides through the guide 1000, one of the notches 1022*a-b* permits the tool support to slide along the axis defined by the guide while the guide is held in a fixed position by the robotic surgical system. The peg extends through one of the notches 1022*a-b* and outside of the guide 1000 and permits the navigation marker attached to the tool support via the peg to be viewed by a navigation camera along an entire range of movement of the tool support through the guide. In some implementations, the peg is utilized without the navigation marker to maintain the orientation of the surgical instrument. In some implementations, the navigation marker is used by navigation camera to track the surgical instrument. The notches 1022*a-b* may constrain movement of the marker in a fixed orientation along the axis defined by the guide. In some implementations, longitudinal notches 1022*a-b* are sized in relation to a peg to permit the surgical instrument to slide along the axis of insertion in reference to the tool support.

Among other things, incorporation of two or more notches, such as notches 1022*a* and 1022*b*, permits for ambidextrous manipulation of the end effector and/or tool. Moreover, it permits positioning of the robotic surgical system on both sides of the operating room table. Furthermore, it permits positioning of the robotic surgical system on both sides of the operating room table in reference to a navigation system (e.g., tracking camera).

In some implementations, the guide 1000 includes one or more input devices, such as electro-mechanical buttons. For example, the guide 100 may include two electromechanical buttons 1008*a* and 1008*b*. In some implementations, the guide 100 includes an activation switch 1060. The activation switch 1060 may be separate from the buttons 1008*a* and 1008*b*. The activation switch 1060 may be a presence detection that can be used for enabling movements of the surgical robot. The types of movements may be defined by the buttons 1008*a* and/or 1008*b*. The present detection may include a long button that is pressed when a user grabs the handle (e.g., to thereby move the handle). In some implementations, the activation switch detects the presence of a hand on the handle.

In some implementations, a user may use the one or more input devices to select to enter a translation mode, positioning mode, axis rotation mode, axis insertion mode and/or axis position mode. In some implementations, the guide 1000 includes an enabling button, rotation button and/or a translation button. In some implementations, the enabling button must be selected with one or more other buttons to enable movement of the end effector. For example, to rotate the end effector, the user may need to select the enabling button and the rotation button. Similarly, to enable translations of the end effector, the user may need to select the enabling button and the translations button. In some implementations, the end effector may enter a course positioning mode when a user selects the enabling button, translations button, or rotations button. In some implementations, selection of the enabling button causes the robotic arm to enter the positioning mode in which the user is able to position the tool appropriately and allows the operator to freely move the robotic arm (e.g., via course movements).

Selection of the translation mode allows, in some implementations, the end effector to be moved along a plane (e.g., a plan in line with the end of a tool such as a drill guide). An operator may use the translation mode to make fine movements with the end effector and to find an entry point. Selection of the rotation mode locks movement of the end effector except rotations (e.g., the manipulator may only be rotated). In some implementations, activation of the rotation mode permits an operator to make fine rotations around an entry point. In axis rotation mode an operator may rotate the end effector around a specific axis (e.g., the axis formed by a drill guide). In axis position mode, an operator may move the end effector without changing an axis (e.g., the axis formed by a drill guide). In axis insertion mode, an operator may move the end effector along a trajectory.

The various positioning modes allow an operator to quickly and accurately move the end effector to a desired position (e.g., on or along a determined trajectory). When all of the buttons are released, in some implementations, the robot actively holds the position of the end effector. For example, if a drill guide is coupled to the end effector, an operator may insert a drill into the drill guide without moving the position of the end effector or drill guide. Thus, after carefully positioning the drill guide along a desired trajectory, an operator may accurately drill along the desired trajectory.

Figure 10B:
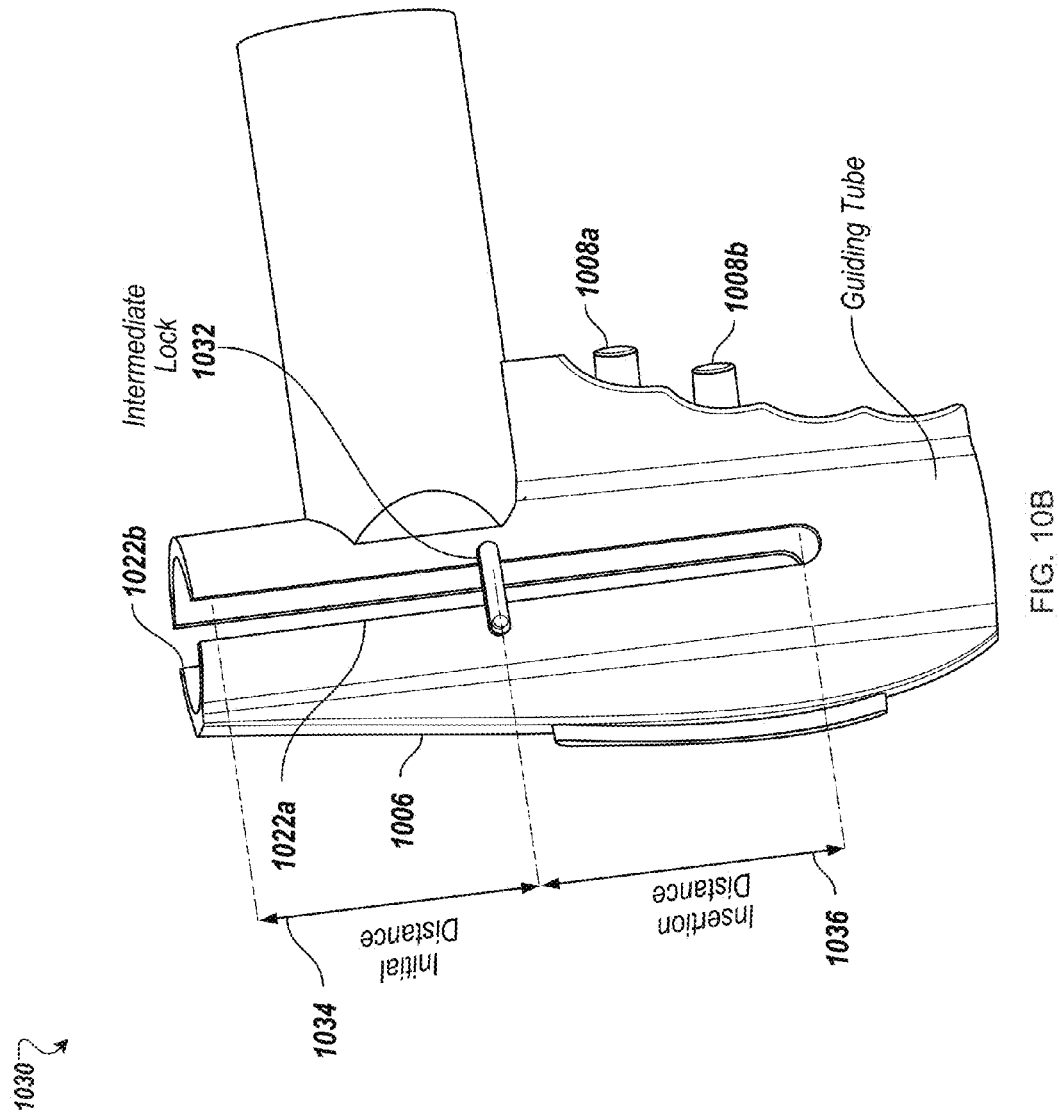
FIG. 10B is an illustration of an example surgical instrument guide with an intermediate lock for use with a robotic surgical system.

FIG. 10B is an illustration of an example surgical instrument guide 1030 with an intermediate lock 1032 to lock the position of the surgical instrument in the guiding tube 1006. Instead of having a long guiding tube, the robot may move the guiding tube 1006 along a trajectory (e.g., in a straight line) thus creating a very long "virtual" guidance without compromising haptic feedback for the surgeon. Additionally, the intermediate lock 1032 enables the surgical instrument to be placed in the guiding tube prior to determining the correct trajectory. After the correct trajectory is determined, the robotic arm may be moved away from the patient such that, for example, the vertebrae may be accessed by a surgeon. After the vertebrae is prepared, the robot can assist the surgeon in finding the right trajectory again, thus significantly decreasing the time necessary for screw placement in comparison to manual spinal surgeries.

An intermediate lock 1032 may be placed at an initial distance 1034, such as 80 mm, from an entry of the guiding tube 1006. In some implementations, the initial distance is 80 mm. In some implementations, the initial distance is between 70-90 mm, 60-80 mm, or 80-100 mm. In some implementations, the initial distance corresponds to the length of the longest pedicle screws used with a small amount of margin) e.g., 5, 10, 15, or 20 mm of margin). In some implementations, the intermediate lock 1032 is a unidirectional lock that only blocks insertion movement. In some implementations, the initial distance 1034 is long enough to allow guidance of the inserted instrument when intermediate lock 1032 is in the locked position. For example, the initial distance, in some implementations, is 30 mm. In some implementations, the initial distance is between 25-25 mm, 20-40 mm, or 35-50 mm. In some implementations, the intermediate lock 1032 is a bidirectional lock that blocks insertion and removal of the surgical instrument.

When the intermediate lock 1032 is released (e.g., unlocked), the surgical instrument may be slide further into the guide. In some implementations, the insertion distance 1036 (e.g., distance the surgical instrument can move forward after the intermediate lock 1032 is released) is selected to allow sufficient guidance of the surgical instrument inside the vertebrae. In some implementations, the insertion distance is 80 mm. In some implementations, the insertion distance is between 70-90 mm, 60-80 mm, or 80-100 mm. This may be defined by the type of surgery and may be, for example, the length of a pedicle screw with some margin (e.g., 40-80 mm of total travel; e.g., 55, 60, 65, 70, or 75 mm total). The intermediate lock 1032 may be implemented using a variety of mechanisms. The intermediate lock 1032 may be a spring lock (e.g., a button that is pressed through a hole on the guide by a spring when the instrument is slide into a particular position). The intermediate lock 1032 may be a small device that blocks the movement of the tool inside the guide 1006. For example, the intermediate lock 1032 may block the peg (e.g., 420 as shown in FIG. 4) that holds a marker (e.g., 412 as shown in FIG. 4) to a tool support (e.g., 410 as shown in FIG. 4). The intermediate lock 1032 may be one or two bars that prevent movement of the instrument unilaterally or bilaterally, respectively. For example, two bars may be used to prevent the peg (e.g., 420 as shown in FIG. 4) from moving. In some implementations, a lock is provided to lock the surgical instrument in place when it is fully inserted in the guide 1006. The lock may be designed and/or function similarly to the intermediate lock.

FIG. 10C is an illustration of an example surgical instrument guide 1150 with an end lock 1052 to lock the position of the surgical instrument in the guiding tube 1006. The end lock may be used to prevent the surgical instrument from accidentally being removed from the guiding tube 1006. In some implementations, an instrument position sensor 1056 (e.g., position detector) is integrated in the guiding tube 1006 (e.g., any guiding tube described herein). The instrument position sensor 1056 may be an inductive sensor, capacitive sensor, resistive sensor, mechanical end switches, optical measuring device, force sensing device, or other similar position sensor. When the surgical instrument is inside the tube 1006, the relative position of the instrument may be measured by the instrument position sensor 1056. In some implementations, the sensor 1056 detects discrete positions of the instrument inside the guiding tube 1006. For example, the sensor 1056 may detect when the surgical instrument is at a top, bottom, or middle position within the guide.

In some implementations, the robot generates movement of the tube 1006 in response to the position of the instrument (e.g., to achieve movement along a desired trajectory). The movement may be generated only when the surgical instrument is at the extremities of the tube 1006 (e.g., at either end of the notch 1022). The combination of these features and the ability to combine movement of the instrument inside the guiding tube 1006 and guidance of the tube 1006 by the robot to provides the ability to obtain long and complicated trajectories using simple and short surgical instrument guide tubes (e.g., 1006) held by the robot.

The end lock 1052 may be a spring lock (e.g., a button that is pressed through a hole on the guide by a spring when the instrument is slide into a particular position). The end lock 1052 may be a small device that blocks the movement of the tool inside the guide 1006. For example, the end lock 1052 may block the peg (e.g., 420 as shown in FIG. 4) that holds a marker (e.g., 412 as shown in FIG. 4) to a tool support (e.g., 410 as shown in FIG. 4). The end lock 1052 may be one or two bars that prevent movement of the instrument unilaterally or bilaterally, respectively. For example, two bars may be used to prevent the peg (e.g., 420 as shown in FIG. 4) from moving.

FIG. 11 is an illustration of an example surgical instrument guide 1100 for use with a robotic surgical system. Guide 1100, in some implementations, includes a rectangular or square structure 1106 (e.g., body), with a longitudinal notch 1108 along its length. In some implementations, the longitudinal notch 1108 is a slot. Other shaped bridges may be used as well, such as hexagonal, trapezoidal, or triangular bodies. The longitudinal notch 1008 is sized in relation to a base 1104 that couples, for example, a tool support 1106. As the base 1104 slides through the guide body 1102, the notch 1108 permits the tool support to slide along the axis defined by the guide while the guide is held in a fixed position by the robotic surgical system. The tool support 1106, in some implementations, is coupled to the base 1104 via an arm 1110 (e.g., peg). The arm 1110 extends through an opening in the notch 1108 and outside of the guide 1100 and permits, for example, the navigation marker attached to the tool support via the arm 1110 to be viewed by a navigation camera along an entire range of movement of the tool support through the guide. In some implementations, the navigation marker is used by navigation camera to track the surgical instrument. The notch 1108 may constrain movement of the marker in a fixed orientation along the axis defined by the guide. In some implementations, longitudinal notch 1108 is sized in relation to a peg to permit the surgical instrument to slide along the axis of insertion in reference to the tool support.

Figure 12:
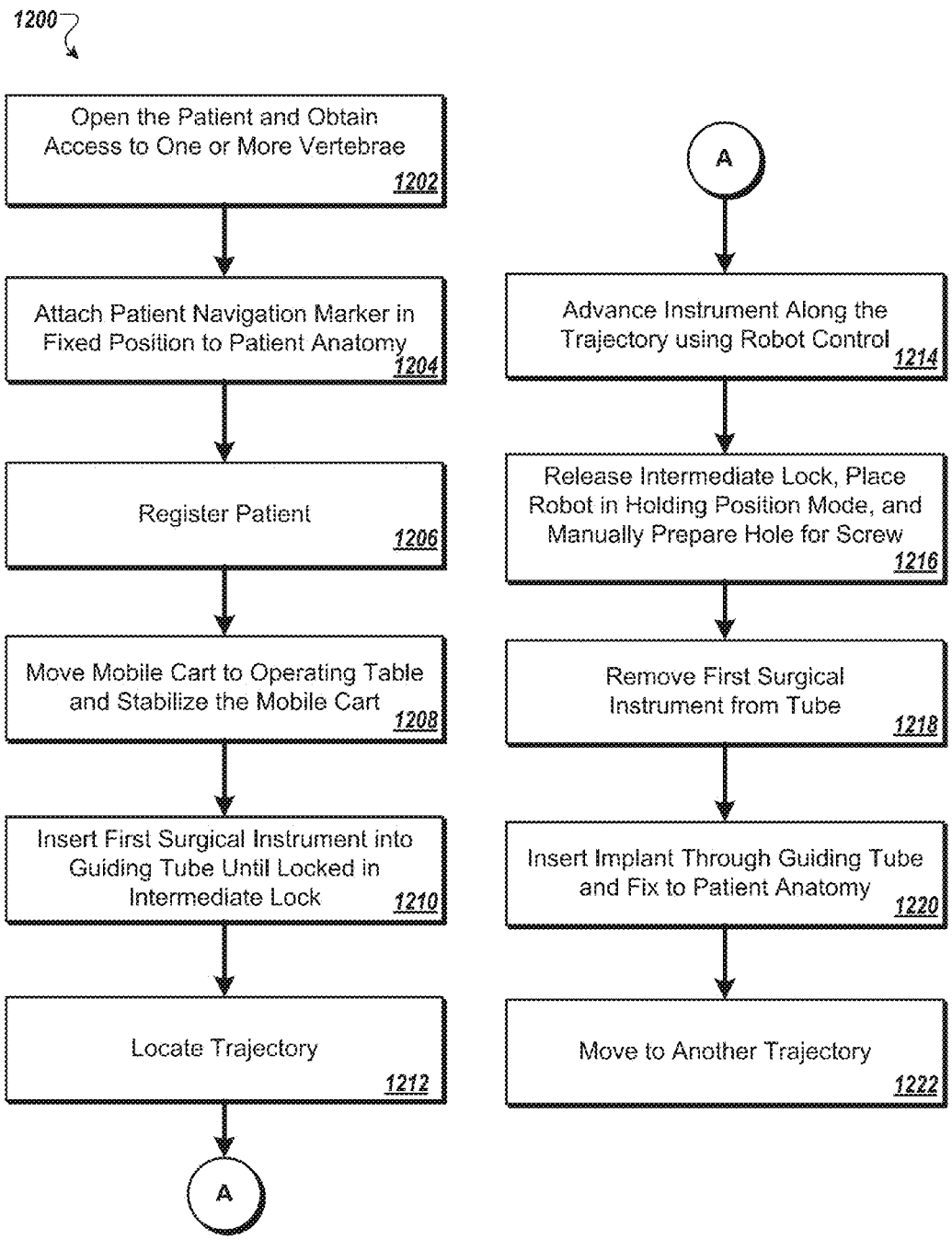
FIG. 12 is a flowchart of an example method for performing surgery with a robotic surgical system.

FIG. 12 is a flowchart of an example method 1200 for performing surgery with a robotic surgical system. The method 1200 may include opening the patient and obtaining access to a vertebra (1202). A patient marker may be attached to the patient in a fixed position (1204) such that any movements of the vertebra may be tracked and compensated for by the robot. The patient may be registered (1206). Patient registration may be accomplished while obtaining intra-operative patient images using 3D fluoroscopy.

The method 1200 may include moving a mobile cart transporting a robotic surgical system comprising a robotic arm in proximity to an operating table and stabilizing the mobile cart (1208). A first surgical instrument may be inserted into the guiding tube until locked in place by the intermediate lock (1210). This allows the robotic arm to be moved while holding the surgical instrument in place. In some implementations, the lock restricts the instrument from being slide past a present position. In some implementations, the lock prevents the instrument from being removed. Various embodiments of the lock are discussed in relation to FIGS. 10B and 10C.

After inserting the surgical instrument, the trajectory may be located (1212). Once the trajectory is located, the instrument may be advanced along the trajectory using robot control (1214). The intermediate lock may be released and the robot may be placed in a holding position mode such that movement of the instrument is restricted along the trajectory, thus allowing a surgeon to manually prepare a hole for a screw (1216). After preparing the hole, the first surgical instrument may be removed from the guidance tube (1218). A second surgical instrument may be inserted after the first instrument is removed. In some implementations, before placing an implant, the user may tap the hole. In some implementations, a self-tapping screw is used directly without drilling. An implant may be inserted through the guiding tube and fixed to the patient anatomy (1220). After fixing the implant to the patient anatomy, the surgeon may move to another trajectory (1222).

Figure 13:
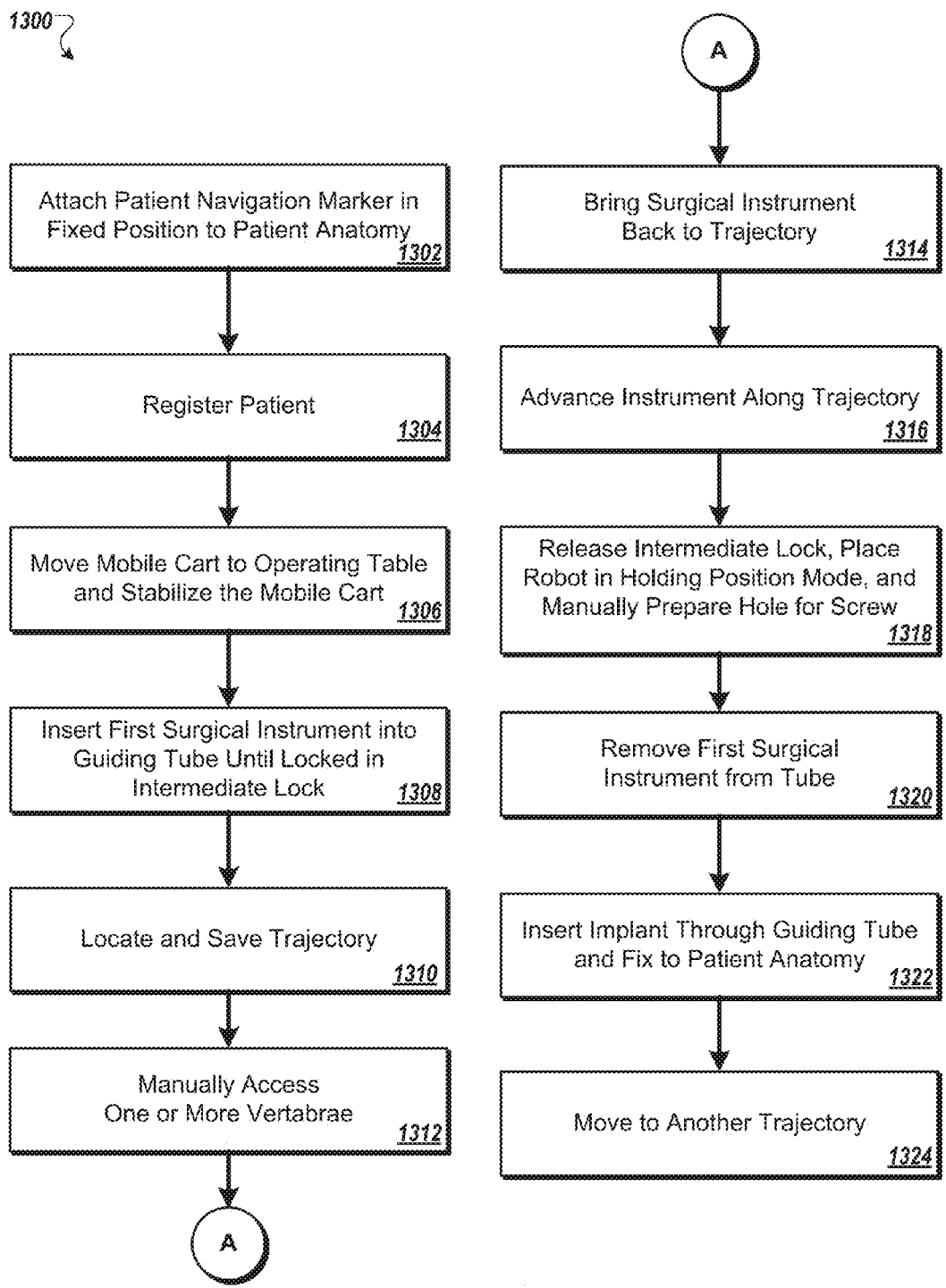
FIG. 13 is a flowchart of an example of a method for performing a minimally invasive surgery using a robotic surgical system as a drill guide.

FIG. 13 is a flowchart of an example of a method 1300 for performing a minimally invasive surgery using a robotic surgical system as a drill guide. A patient marker may be attached to the patient in a fixed position (1302) such that any movements of the vertebra may be tracked and compensated for by the robot. The patient may be registered (1304). Patient registration may be accomplished while obtaining intra-operative patient images using 3D fluoroscopy.

The method 1300 may include moving a mobile cart transporting a robotic surgical system comprising a robotic arm in proximity to an operating table and stabilizing the mobile cart (1306). A first surgical instrument may be inserted into the guiding tube until locked in place by the intermediate lock (1308). This allows the robotic arm to be moved while holding the surgical instrument in place. In some implementations, the lock restricts the instrument from being slide past a present position. In some implementations, the lock prevents the instrument from being removed. Various embodiments of the lock are discussed in relation to FIGS. 10B and 10C.

After inserting the surgical instrument, the trajectory may be located and saved (1310). After saving the trajectory, the vertebra may be manually accessed (1312). The surgical instrument may be brought back to the trajectory (1314). This may be done manually by the surgeon. In some implementations, the surgeon may be assisted and/or guided by the robot to ensure that the instrument is returned to the correct trajectory. For example, an example assistance is the use of a "magnetic" effect which drags the instrument to the correct trajectory and locks it when it is on the correct trajectory.

After aligning the instrument with the trajectory, the instrument may be advanced along the trajectory (1316). The intermediate lock may be released and the robot may be placed in a holding position mode such that movement of the instrument is restricted along the trajectory, thus allowing a surgeon to manually prepare a hole for a screw (1318). After preparing the hole, the first surgical instrument may be removed from the guidance tube (1320). A second surgical instrument may be inserted after the first instrument is removed. An implant may be inserted through the guiding tube and fixed to the patient anatomy (1322). After fixing the implant to the patient anatomy, the surgeon may move to another trajectory (1324).

Figure 14:
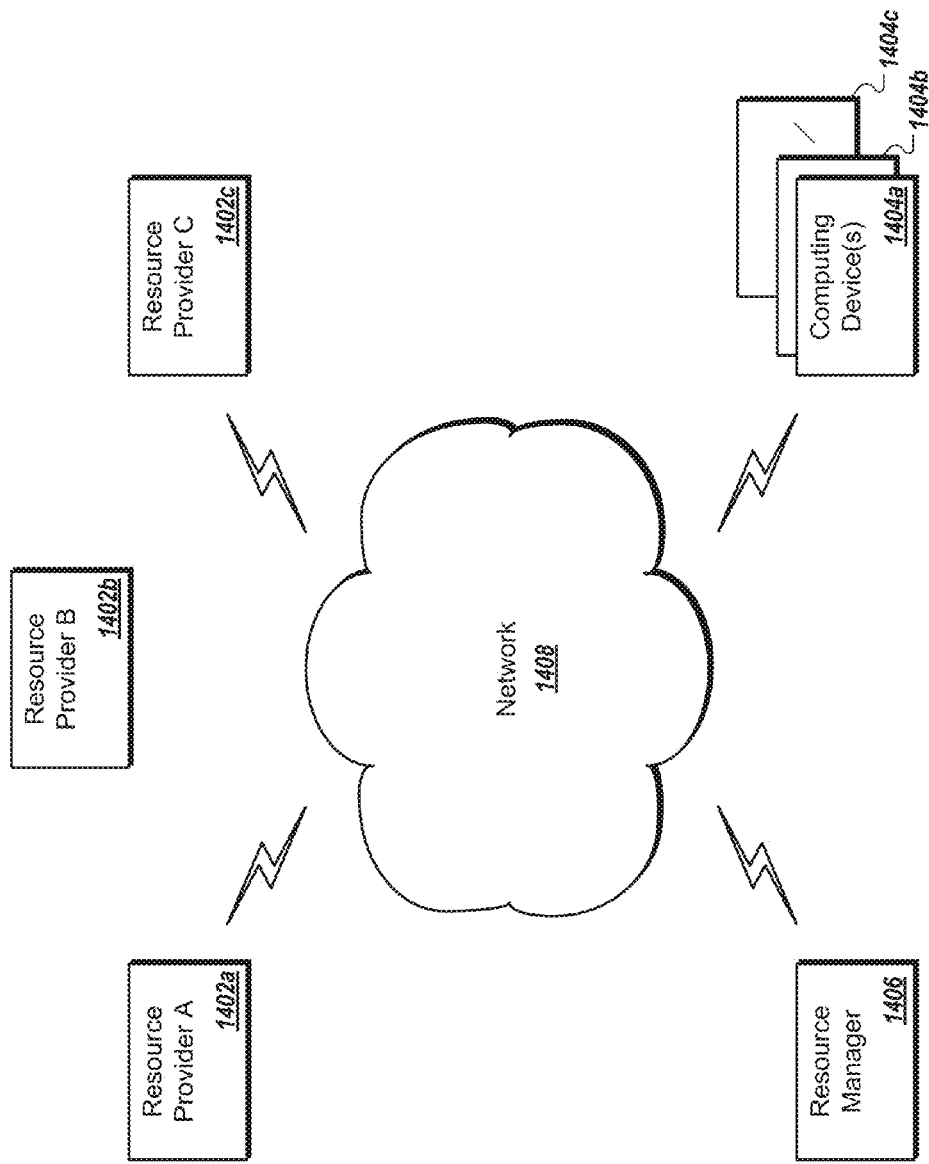
FIG. 14 shows a block diagram of an exemplary cloud computing environment.

As shown in FIG. 14, an implementation of a network environment 1400 for use with a robotic surgical system is shown and described. In brief overview, referring now to FIG. 14, a block diagram of an exemplary cloud computing environment 1400 is shown and described. The cloud computing environment 1400 may include one or more resource providers 1402a, 1402b, 1402c (collectively, 1402). Each resource provider 1402 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 1402 may be connected to any other resource provider 1402 in the cloud computing environment 1400. In some implementations, the resource providers 1402 may be connected over a computer network 1408. Each resource provider 1402 may be connected to one or more computing device 1404a, 1404b, 1404c (collectively, 1404), over the computer network 1408.

The cloud computing environment 1400 may include a resource manager 1406. The resource manager 1406 may be connected to the resource providers 1402 and the computing devices 1404 over the computer network 1408. In some implementations, the resource manager 1406 may facilitate the provision of computing resources by one or more resource providers 1402 to one or more computing devices 1404. The resource manager 1406 may receive a request for a computing resource from a particular computing device 1404. The resource manager 1406 may identify one or more resource providers 1402 capable of providing the computing resource requested by the computing device 1404. The resource manager 1406 may select a resource provider 1402 to provide the computing resource. The resource manager 1406 may facilitate a connection between the resource provider 1402 and a particular computing device 1404. In some implementations, the resource manager 1406 may establish a connection between a particular resource provider 1402 and a particular computing device 1404. In some implementations, the resource manager 1406 may redirect a particular computing device 1404 to a particular resource provider 1402 with the requested computing resource.

Figure 15:
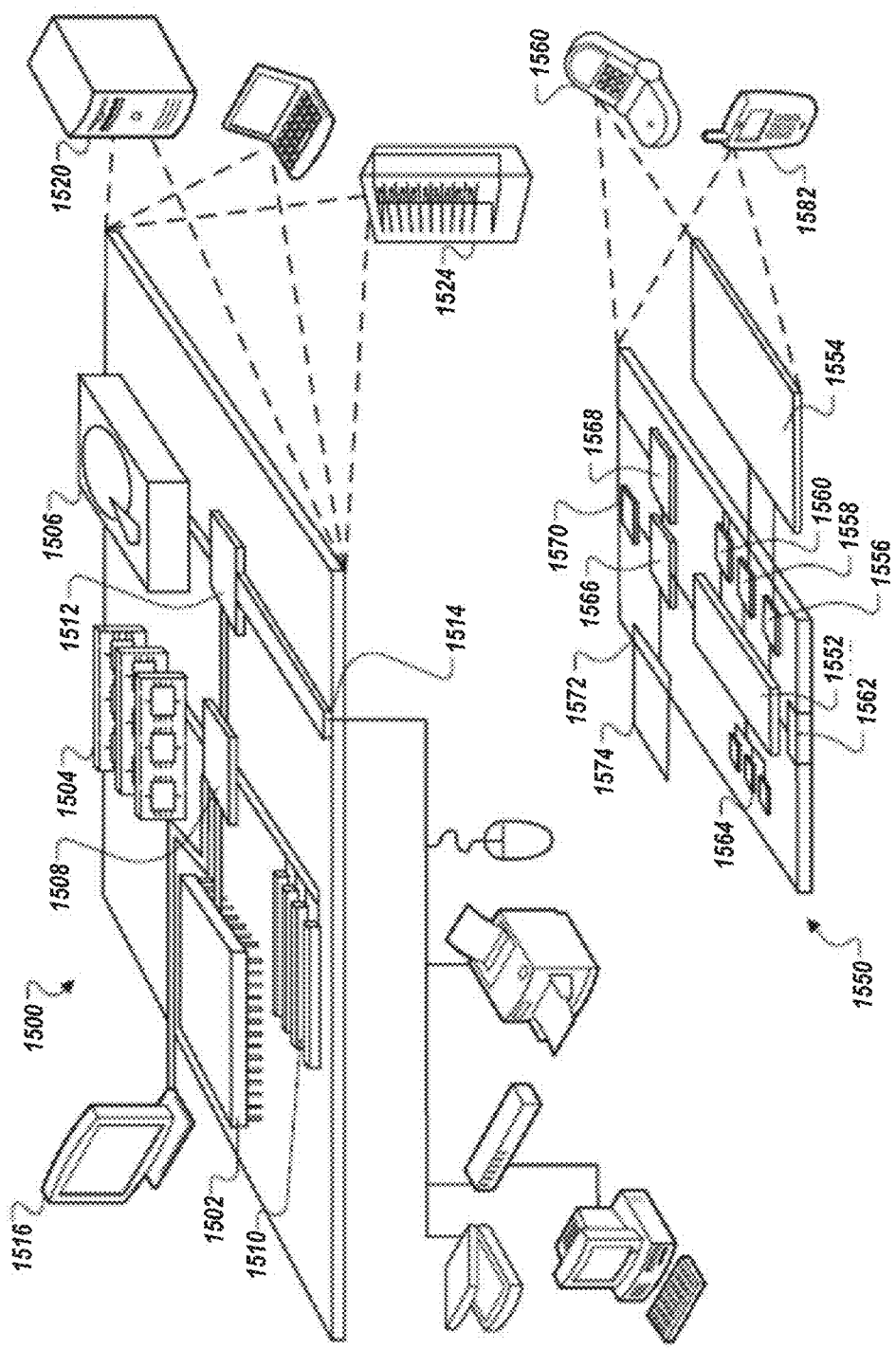
FIG. 15 is a block diagram of a computing device and a mobile computing device.

FIG. 15 shows an example of a computing device 1500 and a mobile computing device 1550 that can be used to implement the techniques described in this disclosure. The computing device 1500 is intended to represent various forms of digital computers, such as laptops, desktops, workstations, personal digital assistants, servers, blade servers, mainframes, and other appropriate computers. The mobile computing device 1550 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 1500 includes a processor 1502, a memory 1504, a storage device 1506, a high-speed interface 1508 connecting to the memory 1504 and multiple high-speed expansion ports 1510, and a low-speed interface 1512 connecting to a low-speed expansion port 1514 and the storage device 1506. Each of the processor 1502, the memory 1504, the storage device 1506, the high-speed interface 1508, the high-speed expansion ports 1510, and the low-speed interface 1512, are interconnected using various busses, and may be mounted on a common motherboard or in other manners as appropriate. The processor 1502 can process instructions for execution within the computing device 1500, including instructions stored in the memory 1504 or on the storage device 1506 to display graphical information for a GUI on an external input/output device, such as a display 1516 coupled to the high-speed interface 1508. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 1504 stores information within the computing device 1500. In some implementations, the memory 1504 is a volatile memory unit or units. In some implementations, the memory 1504 is a non-volatile memory unit or units. The memory 1504 may also be another form of computer-readable medium, such as a magnetic or optical disk.

The storage device 1506 is capable of providing mass storage for the computing device 1500. In some implementations, the storage device 1506 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 1502), perform one or more methods, such as those described above. The instructions can also be stored by one or more storage devices such as computer- or machine-readable mediums (for example, the memory 1504, the storage device 1506, or memory on the processor 1502).

The high-speed interface 1508 manages bandwidth-intensive operations for the computing device 1500, while the low-speed interface 1512 manages lower bandwidth-intensive operations. Such allocation of functions is an example only. In some implementations, the high-speed interface 1508 is coupled to the memory 1504, the display 1516 (e.g., through a graphics processor or accelerator), and to the high-speed expansion ports 1510, which may accept various expansion cards (not shown). In the implementation, the low-speed interface 1512 is coupled to the storage device 1506 and the low-speed expansion port 1514. The low-speed expansion port 1514, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 1500 may be implemented in a number of different forms, as shown in the figure. For example, it may be implemented as a standard server 1520, or multiple times in a group of such servers. In addition, it may be implemented in a personal computer such as a laptop computer 1522. It may also be implemented as part of a rack server system 1524. Alternatively, components from the computing device 1500 may be combined with other components in a mobile device (not shown), such as a mobile computing device 1550. Each of such devices may contain one or more of the computing device 1500 and the mobile computing device 1550, and an entire system may be made up of multiple computing devices communicating with each other.

The mobile computing device 1550 includes a processor 1552, a memory 1564, an input/output device such as a display 1554, a communication interface 1566, and a transceiver 1568, among other components. The mobile computing device 1550 may also be provided with a storage device, such as a micro-drive or other device, to provide additional storage. Each of the processor 1552, the memory 1564, the display 1554, the communication interface 1566, and the transceiver 1568, are interconnected using various buses, and several of the components may be mounted on a common motherboard or in other manners as appropriate.

The processor 1552 can execute instructions within the mobile computing device 1550, including instructions stored in the memory 1564. The processor 1552 may be implemented as a chipset of chips that include separate and multiple analog and digital processors. The processor 1552 may provide, for example, for coordination of the other components of the mobile computing device 1550, such as control of user interfaces, applications run by the mobile computing device 1550, and wireless communication by the mobile computing device 1550.

The processor 1552 may communicate with a user through a control interface 1558 and a display interface 1556 coupled to the display 1554. The display 1554 may be, for example, a TFT (Thin-Film-Transistor Liquid Crystal Display) display or an OLED (Organic Light Emitting Diode) display, or other appropriate display technology. The display interface 1556 may comprise appropriate circuitry for driving the display 1554 to present graphical and other information to a user. The control interface 1558 may receive commands from a user and convert them for submission to the processor 1552. In addition, an external interface 1562 may provide communication with the processor 1552, so as to enable near area communication of the mobile computing device 1550 with other devices. The external interface 1562 may provide, for example, for wired communication in some implementations, or for wireless communication in other implementations, and multiple interfaces may also be used.

The memory 1564 stores information within the mobile computing device 1550. The memory 1564 can be implemented as one or more of a computer-readable medium or media, a volatile memory unit or units, or a non-volatile memory unit or units. An expansion memory 1574 may also be provided and connected to the mobile computing device 1550 through an expansion interface 1572, which may include, for example, a SIMM (Single In Line Memory Module) card interface. The expansion memory 1574 may provide extra storage space for the mobile computing device 1550, or may also store applications or other information for the mobile computing device 1550. Specifically, the expansion memory 1574 may include instructions to carry out or supplement the processes described above, and may include secure information also. Thus, for example, the expansion memory 1574 may be provided as a security module for the mobile computing device 1550, and may be programmed with instructions that permit secure use of the mobile computing device 1550. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 1552), perform one or more methods, such as those described above. The instructions can also be stored by one or more storage devices, such as one or more computer- or machine-readable mediums (for example, the memory 1564, the expansion memory 1574, or memory on the processor 1552). In some implementations, the instructions can be received in a propagated signal, for example, over the transceiver 1568 or the external interface 1562.

The mobile computing device 1550 may communicate wirelessly through the communication interface 1566, which may include digital signal processing circuitry where necessary. The communication interface 1566 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1568 using a radio-frequency. In addition, short-range communication may occur, such as using a Bluetooth®, Wi-Fi™, or other such transceiver (not shown). In addition, a GPS (Global Positioning System) receiver module 1570 may provide additional navigation- and location-related wireless data to the mobile computing device 1550, which may be used as appropriate by applications running on the mobile computing device 1550.

The mobile computing device 1550 may also communicate audibly using an audio codec 1560, which may receive spoken information from a user and convert it to usable digital information. The audio codec 1560 may likewise generate audible sound for a user, such as through a speaker, e.g., in a handset of the mobile computing device 1550. Such sound may include sound from voice telephone calls, may include recorded sound (e.g., voice messages, music files, etc.) and may also include sound generated by applications operating on the mobile computing device 1550.

The mobile computing device 1550 may be implemented in a number of different forms, as shown in the figure. For example, it may be implemented as a cellular telephone 1580. It may also be implemented as part of a smart-phone 1582, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In view of the structure, functions and apparatus of the systems and methods described here, in some implementations, a system and method for performing surgery with a robotic surgical system are provided. Having described certain implementations of methods and apparatus for supporting a robotic surgical system, it will now become apparent to one of skill in the art that other implementations incorporating the concepts of the disclosure may be used. Therefore, the disclosure should not be limited to certain implementations, but rather should be limited only by the spirit and scope of the following claims.

Throughout the description, where apparatus and systems are described as having, including, or comprising specific components, or where processes and methods are described as having, including, or comprising specific steps, it is contemplated that, additionally, there are apparatus, and systems of the disclosed technology that consist essentially of, or consist of, the recited components, and that there are processes and methods according to the disclosed technology that consist essentially of, or consist of, the recited processing steps.

It should be understood that the order of steps or order for performing certain action is immaterial so long as the disclosed technology remains operable. Moreover, two or more steps or actions may be conducted simultaneously.

What is claimed is:

1. A robotic surgical system for performing surgery, the system comprising:

a robotic arm with an end effector comprising a surgical instrument guide configured to hold and/or restrict movement of a surgical instrument there through; and a manipulator configured to allow robotically-assisted or unassisted positioning and/or movement of the surgical instrument guide by a user with at least four degrees of freedom to align an axis defined by the instrument guide at a desired trajectory in relation to a patient situation, wherein the surgical instrument guide comprises a rigid hollow tubular structure having a first open end and a second open end, said structure defining the axis along which movement of a surgical instrument (fitted with a tool support) sliding through the structure is restricted, wherein the tubular structure has an interior surface shaped and sized to accommodate the tool support sliding through the guide such that movement of the tool support is constrained in all directions except along the axis defined by the guide, wherein the tubular structure has an exterior surface comprising at least one flange that is configured for secure coupling of the guide to the end effector of the robotic surgical system, and wherein the tubular structure comprises a longitudinal notch along its length, wherein the longitudinal notch is sized in relation to a peg to (i) permit a navigation marker attached to the tool support via the peg to be viewable by a navigation camera along an entire range of movement of the tool support through the guide, (ii) constrain movement of the marker in a fixed orientation along the axis defined by the guide, and (ii) permit the tool support to slide along the axis defined by the guide while the guide is held in a fixed position by the robotic surgical system.

2. The robotic surgical system of claim 1, wherein the surgical instrument is a member selected from the group consisting of: a drill bit, tap, screw driver, and awl.

3. The robotic surgical system of claim 1, wherein the surgical instrument is a drill bit and the surgical instrument guide is a drill guide.

4. The robotic surgical system of claim 1, wherein the rigid hollow tubular structure is a cylindrical structure.

5. The robotic surgical system of claim 1, wherein the longitudinal notch is a slot.

6. The robotic surgical system of claim 1, wherein the navigation marker is used by navigation camera to track the surgical instrument.

7. The robotic surgical system of claim 1, wherein the longitudinal notch is sized in relation to a peg to permit the surgical instrument to slide along the axis of insertion in reference to the tool support.

8. The robotic surgical system of claim 1, wherein the surgical instrument guide is configured to be used to guide a screw implant and a tissue protector.

9. The robotic surgical system of claim 1, wherein the axis can be aligned with the desired trajectory in relation to the patient situation via the manipulator.

10. The robotic surgical system of claim 1, wherein the surgical instrument guide comprises one or more input devices.

11. The robotic surgical system of claim 1, wherein the surgical instrument guide comprises an activation switch.

* * * * *